US011746366B2

(12) United States Patent
Gibbons et al.

(10) Patent No.: US 11,746,366 B2
(45) Date of Patent: *Sep. 5, 2023

(54) GH5 AND GH30 IN WET MILLING

(71) Applicant: Novozymes A/S, Bagsvaerd (DK)

(72) Inventors: Thomas Patrick Gibbons, Wake Forest, NC (US); Bernardo Vidal, Wake Forest, NC (US); James Lavigne, Wake Forest, NC (US); Michael John Akerman, Wake Forest, NC (US); Xinyu Shen, Wake Forest, NC (US); Yi Cao, Beijing (CN); Wei Li, Beijing (CN); Yu Zhang, Beijing (CN); Soeren Nymand-Grarup, Aabyshoej (DK); Madelyn Mallison Shoup, Raleigh, NC (US); Kenneth Jensen, Oelsted (DK); Kristian Bertel Romer M. Krogh, Bagsvaerd (DK); Lorena Gonzalez Palmen, Malmo (SE)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/628,788

(22) PCT Filed: Jul. 24, 2018

(86) PCT No.: PCT/US2018/043471
§ 371 (c)(1),
(2) Date: Jan. 6, 2020

(87) PCT Pub. No.: WO2019/023222
PCT Pub. Date: Jan. 31, 2019

(65) Prior Publication Data
US 2020/0140909 A1 May 7, 2020

(30) Foreign Application Priority Data
Jul. 24, 2017 (WO) ................ PCT/CN2017/094081

(51) Int. Cl.
| | | |
|---|---|---|
| *C12P 19/14* | (2006.01) | |
| *C08B 30/04* | (2006.01) | |
| *C08B 30/12* | (2006.01) | |
| *C08B 30/16* | (2006.01) | |
| *C12N 9/24* | (2006.01) | |

(52) U.S. Cl.
CPC ............ *C12P 19/14* (2013.01); *C08B 30/044* (2013.01); *C08B 30/12* (2013.01); *C08B 30/16* (2013.01); *C12N 9/248* (2013.01); *C12Y 302/01008* (2013.01)

(58) Field of Classification Search
None
See application file for complete search history.

(56) References Cited

U.S. PATENT DOCUMENTS

| | | | |
|---|---|---|---|
| 5,066,218 A | 11/1991 | Silver | |
| 5,073,201 A * | 12/1991 | Giesfeldt | ................ A23L 33/22 |
| | | | 127/67 |
| 6,566,125 B2 | 5/2003 | Johnston | |
| 2003/0070673 A1 | 4/2003 | Liaw et al. | |
| 2006/0003433 A1 | 1/2006 | Steer | |
| 2007/0059432 A1 | 3/2007 | Norman et al. | |
| 2008/0286435 A1 | 11/2008 | Fukumori et al. | |
| 2012/0244590 A1 | 9/2012 | Lee | |
| 2012/0288900 A1* | 11/2012 | He | .......................... C12P 19/04 |
| | | | 435/99 |
| 2014/0150137 A1 | 5/2014 | Spodsberg | |
| 2016/0040203 A1* | 2/2016 | St. John | ................ C13K 13/002 |
| | | | 435/99 |
| 2016/0257981 A1 | 9/2016 | Long | |
| 2017/0183283 A1 | 6/2017 | Vidal et al. | |
| 2017/0202242 A1* | 7/2017 | Blom | ..................... A23K 20/10 |
| 2020/0009573 A1* | 1/2020 | Vidal, Jr. | ............... A23N 12/00 |

FOREIGN PATENT DOCUMENTS

| | | | |
|---|---|---|---|
| CN | 202626066 | 4/2012 | |
| CN | 102775504 B * | 7/2014 | ............. C08B 30/02 |
| CN | 104448011 | 3/2015 | |
| CN | 104812778 A | 7/2015 | |
| EP | 3167055 B1 | 5/2017 | |
| JP | 05277394 | 11/2008 | |
| WO | 02/00731 A1 | 1/2002 | |
| WO | 02/00911 A1 | 1/2002 | |
| WO | 02/02644 A1 | 1/2002 | |
| WO | 2014/082564 A1 | 6/2014 | |
| WO | 2014/082566 A1 | 6/2014 | |

(Continued)

OTHER PUBLICATIONS

Guo et al., Protein tolerance to random amino acid change, Proc. Natl. Acad. Sci. USA 101, 2004, 9205-10. (Year: 2004).*
Schulein, Cellulases of Trichoderma reesei, Methods Enz. 160, 1988, 234-42. (Year: 1988).*
Miyauchi et al., Expression of a bacterial xylanase in Trichoderma reesei under the egl2 and cbh2 glycosyl hydrolase gene promoters, New Biotechnol. 20, 2013, 523-30. (Year: 2013).*
European Patent Application No. 17151610.7, filed Jan. 16, 2017. (Year: 2017).*
Bier et al., Integrated starch wet milling process, Die Starke 26, 1974, 23-28. (Year: 1974).*

(Continued)

*Primary Examiner* — Todd M Epstein
(74) *Attorney, Agent, or Firm* — David Fazzolare

(57) ABSTRACT

The instant application provides methods to improve the total starch yield and/or gluten yield from corn kernels in a wet milling process, the method comprising admixing corn kernels or a fraction of the corn kernels with an enzyme composition comprising an effective amount of one or more hydrolytic enzymes, wherein at least one of said hydrolytic enzymes is selected from the group consisting of a GH30 polypeptide, a GH5 polypeptide or a combination thereof.

20 Claims, 4 Drawing Sheets

Specification includes a Sequence Listing.

(56) References Cited

FOREIGN PATENT DOCUMENTS

| WO | WO-2014082564 A1 * | 6/2014 | ............. C08B 30/02 |
|----|---------------------|--------|--------------------------|
| WO | 2016/005519 A1 | 1/2016 | |
| WO | 2016/005521 A1 | 1/2016 | |
| WO | 2016/005522 A1 | 1/2016 | |
| WO | 2016095856 A1 | 6/2016 | |
| WO | WO-2017088820 A1 * | 6/2017 | ........... C08B 30/044 |
| WO | 2018/095408 A1 | 5/2018 | |

OTHER PUBLICATIONS

Ramirez et al., Enzymatic corn wet milling: engineering process and cost model, Biotechnol. Biofuels 2, 2009, 2. (Year: 2009).*
Johnston et al., Cereal Chemistry, vol. 81, No. 5, pp. 626-632 (2004).
Doelle et al., Biotechonology, Fundamentals in Biotechnology, vol. IV, pp. 30-32 (2009).
Kantor et al, 2017, UniprotKB No. A0A1Q4FVU7.
Yuki et al., 2014, UniprotKB No. W4QEI7.
Anonymous, 2017, Glycoside Hydrolase Family 30.

* cited by examiner

GH5 AND GH30 IN WET MILLING

CROSS-REFERENCE TO RELATED APPLICATIONS

This application is a 35 U.S.C. 371 national application of international application no. PCT/US2018/043471 filed Jul. 24, 2018, which claims priority or the benefit under 35 U.S.C. 119 of International application no. PCT/CN2017/094081 filed Jul. 24, 2017. The content of these applications is fully incorporated herein by reference.

REFERENCE TO A SEQUENCE LISTING

The contents of the electronic sequence listing created on Jul. 8, 2021, named SQText.txt and 62 KB in size, is hereby incorporated by reference in its entirety.

FIELD OF THE INVENTION

The present invention relates to a method of improving starch and/or gluten yield from corn kernels in a wet milling process, by contacting said corn kernels with an enzyme composition comprising a GH30 polypeptide, a GH5 polypeptide or a combination thereof, preferably during fiber washing.

BACKGROUND OF THE INVENTION

Conventional wet milling of corn is a process designed for the recovery and purification of starch and several coproducts including germ, gluten (protein) and fiber. Fiber is the least valuable coproduct, so the industry has put substantial effort into increasing the yield of the more valuable products, such as starch and gluten, while decreasing the fiber fraction. High quality starch is valuable as it can be used for a variety of commercial purposes after further processing to products such as dried starch, modified starch, dextrins, sweeteners and alcohol. Gluten is usually used for animal feed, as corn gluten meal (Around 60% protein) or corn gluten feed (Around 20% protein).

The wet milling process can vary significantly dependent on the specific mill equipment used, but usually the process include: grain cleaning, steeping, grinding, germ separation, a second grinding, fiber separation, gluten separation and starch separation. After cleaning the corn kernels, they are typically softened by soaking in water or in a dilute $SO_2$ solution under controlled conditions of time and temperature. Then, the kernels are grinded to break down the pericarp and the germ is separated from the rest of the kernel. The remaining slurry, mainly consisting of fiber, starch and gluten is finely ground and screened in a fiber washing process, to separate the fiber from starch and gluten, before the gluten and starch is separated and the starch can be purified in a washing/filtration process.

The use of enzymes in several steps of the wet milling process has been suggested, such as the use of enzymes for the steeping step of wet milling processes. The commercial enzyme product STEEPZYME® (available from NOVOZYMES A/S) has been shown suitable for the first step in wet milling processes, i.e., the steeping step where corn kernels are soaked in water.

More recently, "enzymatic milling", a modified wet milling process that uses proteases to significantly reduce the total processing time during corn wet milling and eliminates the need for sulfur dioxide as a processing agent, has been developed. Johnston et al., *Cereal Chem,* 81, p. 626-632 (2004).

U.S. Pat. No. 6,566,125 discloses a method for obtaining starch from maize involving soaking maize kernels in water to produce soaked maize kernels, grinding the soaked maize kernels to produce a ground maize slurry, and incubating the ground maize slurry with enzyme (e.g., protease).

U.S. Pat. No. 5,066,218 discloses a method of milling grain, especially corn, comprising cleaning the grain, steeping the grain in water to soften it, and then milling the grain with a cellulase enzyme.

WO 2002/000731 discloses a process of treating crop kernels, comprising soaking the kernels in water for 1-12 hours, wet milling the soaked kernels and treating the kernels with one or more enzymes including an acidic protease.

WO 2002/000911 discloses a process of starch gluten separation, comprising subjecting mill starch to an acidic protease.

WO 2002/002644 discloses a process of washing a starch slurry obtained from the starch gluten separation step of a milling process, comprising washing the starch slurry with an aqueous solution comprising an effective amount of acidic protease.

WO 2014/082566 and WO 2014/082564 disclose cellulolytic compositions for use in wet milling.

While the art has investigated the effect of using enzymes in corn wet milling, during steeping/soaking of corn kernels, during grinding of the corn kernels, and in starch gluten separation, there is still a need for improved enzyme technology that may lower the energy expenditure and costs associated with corn wet milling and provide increased yield of starch and gluten.

SUMMARY OF THE INVENTION

In a first aspect the present invention relates to a method to improve the total starch yield and/or gluten yield that can be obtained from corn kernels in a wet milling process, the method comprising: Admixing corn kernels or a fraction of the corn kernels with an enzyme composition comprising an effective amount of one or more hydrolytic enzymes, wherein at least one of said hydrolytic enzymes is selected from the group consisting of a GH30 polypeptide, a GH5 polypeptide and a combination thereof.

In a second aspect, the present invention relates to an enzyme composition comprising an isolated GH30 polypeptide, an isolated GH5 polypeptide or both, as well as the use of such an enzyme compositions to improve the total starch yield and/or gluten yield that can be obtained from corn kernels in a wet milling process.

In a third aspect, the present invention relates to compositions comprising corn starch, corn gluten or corn fiber, said compositions being obtainable by the method described in a first aspect and in embodiments of the invention.

In other aspects the present invention relates to polypeptides having xylanase activity and polynucleotides encoding the polypeptides.

In a fourth aspect the invention relates to isolated polypeptides having xylanase activity, selected from the group consisting of:
  (a) A polypeptide having at least 80% sequence identity to the mature polypeptide of SEQ ID NO: 10 or 12;
  (b) A polypeptide encoded by a polynucleotide having at least 80% sequence identity to the mature polypeptide coding sequence of SEQ ID NO: 9 or SEQ ID NO: 11;

(c) A variant of the mature polypeptide of SEQ ID NO: 10 or 12 comprising a substitution, selection and/or insertion at one or more positions; and (d) A fragment of the polypeptide of (a), (b), or (c) having xylanase activity.

In a fifth aspect, the invention relates to a composition comprising a polypeptide according to the fourth aspect of the invention.

The invention also relates to nucleic acid constructs or expression vectors comprising a polynucleotide encoding a polypeptide of the fourth aspect of the invention operably linked to one or more control, sequences that directs the production of the polypeptide in an expression host.

BRIEF DESCRIPTION OF THE FIGURES

The present invention and in particular preferred embodiments according to the invention will be described in more detail with reference to the accompanying figures. The figures show ways of implementing the present invention and are not to be construed as being limiting to other possible embodiments falling within the scope of the attached claim set.

DETAILED DESCRIPTION

Figure 1:
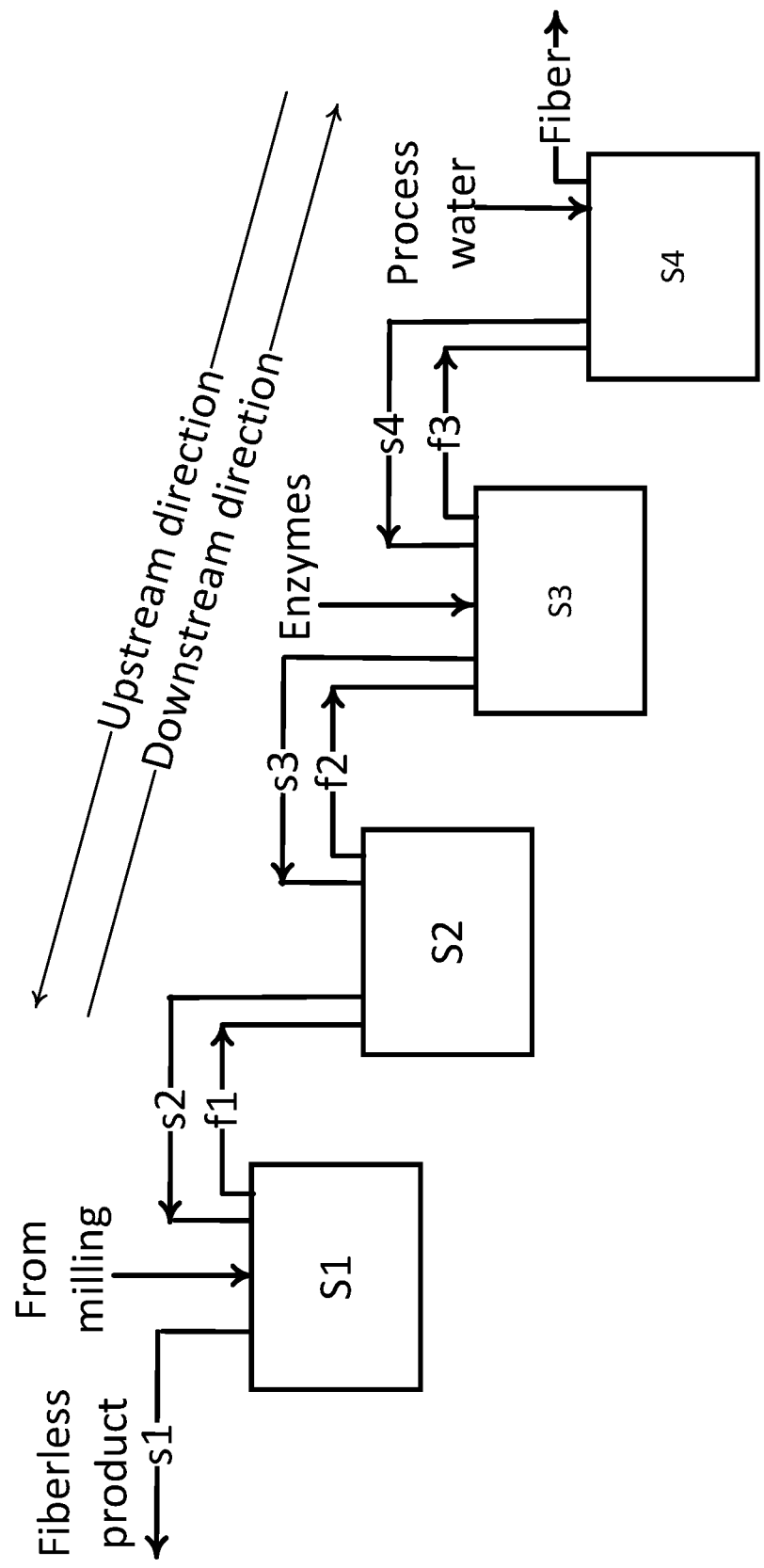
FIG. 1 schematically illustrates a first embodiment of a counter current fiber wash system according to present invention, FIG. 2 schematically illustrates a further embodiment of a system according to the present invention.

It is an object of the present invention to provide a method to improve the starch and/or gluten yields that can be obtained from corn kernels in a wet milling process, by treating the corn kernels with a hydrolytic enzyme composition, preferably during the fiber washing procedure. The inventors of the present invention has surprisingly found that the enzymatic treatment of corn kernels with a GH5 polypeptide or a GH30 polypeptide or a combination thereof, improve the release of bound starch and gluten from fiber and thus improve the starch and/or gluten yields that can be obtained.

The Wet Milling Process:

Corn kernels are wet milled in order to open up the kernels and separate the kernels into its four main constituents: starch, germ, fiber and gluten.

The wet milling process can vary significantly from mill to mill, however conventional wet milling usually comprises the following steps:

1. Steeping and germ separation,
2. Fiber washing procedure
3. Starch/gluten separation, and
4. Starch washing.

1. Steeping, Grinding and Germ Separation

Corn kernels are softened by soaking in water for between about 30 minutes to about 48 hours, preferably 30 minutes to about 15 hours, such as about 1 hour to about 6 hours at a temperature of about 50° C., such as between about 45° C. to 60° C. During steeping, the kernels absorb water, increasing their moisture levels from 15 percent to 45 percent and more than doubling in size. The optional addition of e.g. 0.1 percent sulfur dioxide ($SO_2$) and/or $NaHSO_3$ to the water prevents excessive bacteria growth in the warm environment. As the corn swells and softens, the mild acidity of the steepwater begins to loosen the gluten bonds within the corn and release the starch. After the corn kernels are steeped they are cracked open to release the germ. The germ contains corn oil. The germ is separated from the heavier density mixture of starch, gluten and fiber essentially by "floating" the germ segment free of the other substances under closely controlled conditions. This method serves to eliminate any adverse effect of traces of corn oil in later processing steps.

2. Fiber Washing Procedure

To get maximum starch and gluten recovery, while keeping any fiber in the final product to an absolute minimum, it is necessary to wash the free starch and gluten from the fiber during processing. The fiber is collected, slurried and screened to reclaim any residual starch or gluten.

3. Starch Gluten Separation

The starch-gluten suspension from the fiber-washing step, called mill starch, is separated into starch and gluten. Gluten has a low density compared to starch. By passing mill starch through a centrifuge, the gluten is readily spun out.

4. Starch Washing

The starch slurry from the starch separation step contains some insoluble protein and much of solubles. They have to be removed before a top quality starch (high purity starch) can be made. The starch, with just one or two percent protein remaining, is diluted, washed 8 to 14 times, re-diluted and washed again in hydroclones to remove the last trace of protein and produce high quality starch, typically more than 99.5% pure.

Products of wet milling: Wet milling can be used to produce, without limitation, corn steep liquor, corn gluten feed, germ, corn oil, corn gluten meal, corn starch, modified corn starch, syrups such as corn syrup, and corn ethanol.

Definition of Enzymes:

Cellulolytic enzyme or cellulase/polypeptide with cellulase activity or cellulolytic activity: The terms "cellulolytic enzyme", "cellulase" and polypeptide with cellulase activity or cellulolytic activity are used interchangeably herein and refer to one or more (e.g., several) enzymes that hydrolyze a cellulosic material, which comprise any material comprising cellulose, such as fiber. Cellulolytic enzymes include endoglucanase(s) (E.C 3.2.1.4), cellobiohydrolase(s) (E.C 3.2.1.91 and E.C 3.2.1.150), beta-glucosidase(s) (E.C. 3.2.1.21), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including WHATMAN No1 filter paper, microcrystalline cellulose, bacterial cellulose, algal cellulose, cotton, pretreated lignocellulose, etc. The most common total cellulolytic activity assay is the filter paper assay using WHATMAN No1 filter paper as the substrate. The assay was established by the International Union of Pure and Applied Chemistry (IUPAC) (Ghose, 1987, *Pure Appl. Chem.* 59: 257-68).

Cellulolytic enzyme activity can also be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 40° C., 45° C., 50° C., 55° C., 60° C., 65° C., 70° C., 75° C., or 80° C., and a suitable pH, such as 4-9, e.g., 4.0, 4.5, 5.0, 5.5, 6.0, 6.5, 7.0, 7.5, 8.0, 8.5, or 9.0, compared to a control hydrolysis without addition of cellulolytic enzyme protein. Typical conditions are 1 ml reactions, washed or unwashed PCS, 5% insoluble solids (dry weight), 50 mM sodium acetate 5 pH 5, 1 mM MnSO4, 50° C., 55° C., or 60° C., 72 hours, sugar analysis by AMINEX® HPX-87H column chromatography (Bio-Rad Laboratories, Inc., Hercules, Calif., USA).

Hydrolytic enzymes or hydrolase/polypeptide with hydrolase activity: "Hydrolytic enzymes" and polypeptide with hydrolase activity are used interchangeably herein and refer to any catalytic protein that use water to break down substrates. Hydrolytic enzymes include cellulases (EC 3.2.1.4), xylanases (EC 3.2.1.8) arabinofuranosidases (EC 3.2.1.55 (Non-reducing end alpha-L-arabinofuranosidases); EC 3.2.1.185 (Non-reducing end beta-L-arabinofuranosidases) cellobiohydrolase I (EC 3.2.1.150), cellobiohydrolase II (E.C. 3.2.1.91), cellobiosidase (E.C. 3.2.1.176), beta-glucosidase (E.C. 3.2.1.21), beta-xylosidases (EC 3.2.1.37).

Xylanases/polypeptide with xylanase activity: The terms "xylanase" and polypeptide with xylanase activity are used interchangeably herein and refer to a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as the amount of xylanase activity that produces 1.0 µmole of azurine per minute at 37° C., pH 6 from 0.2% AZCL-arabinoxylan as substrate in 200 mM sodium phosphate pH 6.

Other Definitions

In the present context, terms are used in manner being ordinary to a skilled person. Some of these terms are elucidated below:

Contact time: For one or more enzymes to react with a substrate, the one or more enzymes have to be in contact with the substrate. "Contact time" refers to the time period in which an effective amount of one or more enzymes is in contact with at least a fraction of a substrate mass. The enzymes may not be in contact with all of the substrate mass during the contact time, however mixing the one or more enzymes with a substrate mass allows the potential of enzymatically catalyzed hydrolysis of a fraction of the substrate mass during the contact time.

Corn kernel: A variety of corn kernels are known, including, e.g., dent corn, flint corn, pod corn, striped maize, sweet corn, waxy corn and the like.

Some corn kernels has an outer covering referred to as the "Pericarp" that protects the germ in the kernels. It resists water and water vapour and is undesirable to insects and microorganisms. The only area of the kernels not covered by the "Pericarp" is the "Tip Cap", which is the attachment point of the kernel to the cob.

Corn kernels or a fraction of the corn kernels: This term is used to describe the corn kernels through the process of wet milling. When the corn kernels are broken down and processed, all fractionated parts of the corn kernel are considered to be included when this term is used. The term include for example: soaked kernels, grinded kernels, corn kernel mass, a first fraction, a second fraction, one or more fractions of the corn kernel mass ect.

Corn kernel mass: is preferably used to reference a mass comprising fiber, gluten and starch, preferably achieved by steaming and grinding crop kernels and separating a mass comprising fiber, gluten and starch from germs. As the corn kernel mass move through the fiber washing, it is separated into several fractions, including a first fraction (s) and a second fraction (f). Hence, "fractions of corn kernel mass" and "one or more fractions of corn kernel mass" refer inter alia to these first (s) and second fractions (f).

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide, wherein the fragment has pectin lyase activity.

Germ: The "Germ" is the only living part of the corn kernel. It contains the essential genetic information, enzymes, vitamins, and minerals for the kernel to grow into a corn plant. In yellow dent corn, about 25 percent of the germ is corn oil. The endosperm covered or surrounded by the germ comprises about 82 percent of the kernel dry weight and is the source of energy (starch) and protein for the germinating seed. There are two types of endosperm, soft and hard. In the hard endosperm, starch is packed tightly together. In the soft endosperm, the starch is loose.

GH5 polypeptide: refers to a polypeptide with enzyme activity, the polypeptide being classified as member of the Glycoside hydrolase family 5 in the database of Carbohydrate-Active enZYmes (CAZymes) (http://www.cazy.org/).

GH30 polypeptide: refers to a polypeptide with enzyme activity, the polypeptide being classified as member of the Glycoside hydrolase family 30 in the database of Carbohydrate-Active enZYmes (CAZymes) (http://www.cazy.org/).

Gluten: Gluten is a protein, made up from two smaller proteins, glutenin and gliadin. Herein "gluten" refers to the majority of proteins found in corn kernels. The major products of gluten from corn wet milling is corn gluten meal (Approximately 60% protein) and corn gluten feed (Approximately 20% protein).

Grind or grinding: The term "grinding" refers to breaking down the corn kernels into smaller components.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Incubation time: Time in which the one or more fractions of the corn kernel mass is in contact with hydrolytic enzyme during fiber washing, without being screened.

In many preferred embodiments, a method according to the present invention utilises a system comprising a space (V), or "incubator", inside which the material is "left to be affected" by the enzymes and in such situations, the incubation time may be determined by:

$$t_{it} = \frac{\text{volume of incubator } [m^3] * \text{density of inflow to incubator } [kg/m^3]}{\text{mass inflow per time unit to the incubator } [kg/s]}$$

Alternatively, if the inflow to the incubator is expressed in terms of volume per time unit:

$$t_{it} = \frac{\text{volume of incubator } [m^3]}{\text{volume inflow per time unit to the incubator } [m^3/s]}$$

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 21 to 678 of SEQ ID NO: 2 based on the computer program SignalP (Nielsen et al., 1997, *Protein Engineering* 10: 1-6) that predicts amino acids 1 to 20 of SEQ ID NO: 2 are a signal peptide. It is known in the art that a host cell may produce a mixture of two or more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide.

Mill equipment: "Mill equipment" refers to all equipment used on a mill. The wet milling process will vary dependent on the available mill equipment. Examples of mill equipment can be steeping tanks, evaporator, screw press, rotatory dryer, dewatering screen, centrifuge, hydrocyclone ect. The size, and number of each mill equipment/milling lines can vary on different mills, which will affect the milling process. For example, the number of fiber washing screen units can vary and so can the size of a centrifuge.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Retention time: The time in which one or more hydrolytic enzymes and corn kernels or a fraction of the corn kernels are allowed to react during the fiber washing procedure.

In some embodiments, the retention time is the time period in which the corn kernel mass, received in the first screen unit (S1) and one or more fractions thereof, are contacted with an effective amount of one or more hydrolytic enzymes before leaving the fiber washing system again. During the retention time, the one or more fractions of corn kernel mass is incubated with one or more hydrolytic enzymes in a space (V), before it leaves the fiber washing system, as part of a first fraction (s1) from the most upstream screen unit (S1) or as part of a second fraction (f4) from the most downstream screen unit (S4).

Retention time may preferably be estimated as the average duration of time solid matter spends in a fiber washing system as defined in relation to the present invention. This may be estimated by the following relation:

$$t_{rt} = \frac{\text{volume of system: } [m^3] * \text{density of mass inflow } [kg/m^3]}{\text{mass inflow per time unit to the system } [kg/s]}$$

Alternatively, if the inflow to the system is expressed in terms of volume per time unit:

$$t_{it} = \frac{\text{volume of system } [m^3]}{\text{volume inflow per time unit to the system } [m^3/s]}$$

The volume of the system is typically set equal to the sum of the volumes of all voids in the system; however, as the tubing in the system typically is made small, it may be preferred to disregard the volume of the tubing.

Screened: The term "screened" or "screening" refers to the process of separating corn kernel mass into a first fraction s and a second fraction f and movement of these fractions from one screen unit to another. A non-screening period is a non-separating period provided for incubation of corn kernel mass or fractions thereof with enzymes.

Sequence identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. Version 6.1.0 was used.

The optional parameters used are gap open penalty of 10, gap extension penalty of 0.5, and the EBLOSUM62 (EMBOSS version of BLOSUM62) substitution matrix. The output of Needle labelled "longest identity" (obtained using the -nobrief option) is used as the percent identity and is calculated as follows: (Identical Residues×100)/(Length of Alignment−Total Number of Gaps in Alignment).

Starch: The term "starch" means any material comprised of complex polysaccharides of plants, composed of glucose units that occurs widely in plant tissues in the form of storage granules, consisting of amylose and amylopectin, and represented as $(C_6H_{10}O_5)n$, where n is any number.

Steeping or soaking: The term "steeping" means soaking the crop kernel with water and optionally $SO^2$.

Description of the invention: An aspect of the present invention is to provide a method to improve the total starch yield and/or gluten yield that can be obtained from corn kernels in a wet milling process, the method comprising: Admixing corn kernels or a fraction of the corn kernels with an enzyme composition comprising an effective amount of one or more hydrolytic enzymes, wherein at least one of said hydrolytic enzymes is selected from the group consisting of a GH30 polypeptide, a GH5 polypeptide or a combination thereof.

Some of the starch and/or gluten in corn kernels or fractions of corn kernels, may be bound to the fiber fraction and never released during the wet milling process. However, addition of hydrolytic enzymes, which may include any catalytic protein that can use water to break down substrates present in corn kernels, may release some of the bound starch and/or gluten and thus improve the total yield of starch and/or gluten in the wet milling process. The present inventors has surprisingly found that GH5 polypeptides and GH30 polypeptides are particularly effective in decreasing the amount of bound starch and gluten in the fiber fraction.

In one embodiment, the method of the present invention leads to an increase in the amount of starch and/or gluten released from fiber during the process, such as during the fiber washing procedure.

The specific procedure and the equipment used in the wet milling process can vary, but the main principles of the process remains the same (See description on wet milling process).

In one embodiment, the method of the invention comprise the steps of:
a) soaking the corn kernels in water to produce soaked kernels;
b) grinding the soaked kernels to produce soaked and ground kernels;
c) separating germs from the soaked and ground kernels to produce a corn kernel mass comprising fiber, starch and gluten; and
d) subjecting the resultant corn kernel mass to a fiber washing procedure.

To get maximum starch and gluten recovery, while keeping any fiber in the final product to an absolute minimum, it is necessary to wash the free starch and gluten from the fiber fraction during processing. The fiber is collected, slurried and screened, typically after soaking, grinding and separation of germs from the corn kernels (See description of wet milling process), to reclaim any residual starch or gluten in the corn kernel mass. This process is herein referred to as the fiber washing procedure.

In one embodiment, said corn kernels or a fraction of said corn kernels is admixed with said one or more hydrolytic enzymes, before, during or after the step of subjecting the corn kernel mass to a fiber washing procedure.

In one embodiment, said corn kernels or a fraction of said corn kernels are admixed with said one or more hydrolytic enzymes, before the step of subjecting the corn kernel mass to a fiber washing procedure. According to this embodiment, the corn kernels are preferably admixed with said one or more hydrolytic enzymes during steeping during grinding and/or during germ separation.

In one embodiment, said corn kernels or a fraction of said corn kernels is admixed with said one or more hydrolytic enzymes, after the step of subjecting the corn kernel mass to a fiber washing procedure.

In a preferred embodiment, said corn kernels or a fraction of said corn kernels is admixed with said one or more hydrolytic enzymes during the step of subjecting the corn kernel mass to a fiber washing procedure.

In one embodiment, said corn kernels or a fraction of said corn kernels is allowed to react with said one or more hydrolytic enzymes for at least 15 minutes, such as at least 20 minutes, at least 25 minutes, at least 30 minutes, at least 35 minutes, at least 40 minutes, at least 45 minutes, at least 50 minutes, at least 55 minutes, at least 60 minutes, at least 70 minutes, at least 80 minutes, at least 90 minutes, at least 100 minutes, at least 110 minutes or at least 120 minutes.

The specific equipment used in the fiber washing procedure can vary, but the main principle of the process remains the same.

In one embodiment, said fiber washing procedure comprise the use of a fiber washing system optimized for introduction of one or more hydrolytic enzymes, wherein the fiber washing system comprise a space (V) configured to provide a total reaction time in the fiber washing system (retention time) of at least 35 minutes, such as at least 40 minutes, at least 45 minutes, at least 50 minutes, at least 60 minutes, at least 70 minutes, at least 80 minutes, at least 90 minutes, at least 100 minutes, at least 110 minutes or at least 120 minutes and less than 48 hours, such as less than 40 hours, less than 36 hours, less than 30 hours, less than 24 hours, less than 20 hours, less than 12 hours, less than 10 hours, less than 8 hours, less than 6 hours, less than 5 hours, less than 4 hours, less than 3 hours. In one embodiment the total retention time in the fiber washing system is between 35 minutes and 48 hours such as between 35 minutes and 24 hours, 35 minutes and 12 hours, 35 minutes and 6 hours, 35 minutes and 5 hours, 35 minutes and 4 hours, 35 minutes and 3 hours, 35 minutes and 2 hours, 45 minutes and 48 hours, 45 minutes and 24 hours, 45 minutes and hours, 45 minutes and 6 hours, 45 minutes and 5 hours, 45 minutes and 4 hours, 45 minutes and 3 hours, 45 minutes and 2 hours 1-48 hours, 1-24 hours, 1-12 hours, 1-6 hours, 1-5 hours, 1-4 hours, 1-3 hours, 1-2 hours.

In one embodiment, the fiber washing system comprises:
a plurality of screen units (S1 . . . S4) being fluidly connected in a counter current washing configuration; each screen unit being configured for separating a stream of corn kernel mass and liquid into two fractions: a first fraction (s) and a second fraction (f), said second fraction (f) containing a higher amount measured in wt % fiber than the first fraction (s);
a space (V) arranged in the system and being fluidly connected to receive said first fraction (s), said second fraction (f), or a mixed first and second fraction (s,f), preferably only a second fraction (f), and configured to provide an incubation time for one or both fractions received in the space; and outletting the thereby incubated one or both fractions to a downstream screen unit (S4),
wherein the system is configured for
inletting corn kernel mass and liquid to the most upstream screen unit (S1)
outletting the first fraction (s1) from the most upstream screen unit (S1) as a product stream containing starch,
inletting process water, preferably arranged for inletting process water to a most downstream screen unit (S4),
outletting the second fraction (f4) from most downstream screen unit (S4) as a washed corn kernel mass containing a lower amount of starch and gluten than the original corn kernel mass.
introducing hydrolytic enzymes into the system.

FIG. 1 schematically illustrates an embodiment of a fiber washing system as described above. As illustrated in FIG. 1, the fiber washing system comprises a plurality of screen units S1, S2, S3, S4 being fluidly connected in a counter current washing configuration. "Fluidly connected" typically means that the screen units are connected by use of flow lines, such as pipes for transporting matter between the screen units. Each of the screen units S1-S4 is configured for separating a stream of corn kernel mass and liquid into two fractions: a first fraction s (s1, s2, s3, s4) and a second fraction f (f1, f2, f3, f4). As the skilled person will understand, the number of first fractions produced in the fiber washing system depends on the number screen units included in the system. The number of screen units in the system is preferably between 2-8, and in such embodiments the number of firsts and second fractions will also be between 2-8. The screen units are typically configured so that the solid matter is separated out in a separate stream whereby the second fraction f contains a higher amount measured in wt % fiber than the first fraction s. In the figure, notation "s" preferably refers to a fibreless stream (containing starch) and notation "f" preferably refers to a fiber containing stream. Index on f and s refers to the origin of the stream. It is noted that although it is preferred that the first fractions s does not contain any fiber, this may in a practical set-up be difficult to achieve.

The flow in the system has a downstream direction and an upstream direction: each screen unit; e.g. screen unit S3, receives a stream; e.g. f2, from an upstream screen unit, e.g. S2 and delivers a stream; e.g. s3, to the upstream screen unit; e.g. S2. Similarly, the screen unit S3 receives a stream s4 from a downstream screen unit S4 and delivers a stream f3 to the downstream screen unit S4.

As illustrated in FIG. 1, process water, that is typically water that is used as washing water in the system, is provided to the most downstream screen unit S4, and the process water is typically water not containing fiber. Corn kernel mass is typically a liquid suspension (typically a suspension in water), provided at the most upstream screen unit S1. This is in FIG. 1 indicated by the arrow labelled "From milling". Thereby, and by the fluid connection between the screen units, the corn kernel mass and fractions f thereof flow downstream in the system and the process water moves upstream in the system. Thus, the fluid configuration in the system can be seen as the corn kernel mass is washed in the most upstream screen unit S1 by a fluid containing high amount of starch and in the most downstream screen unit S4 washed by a fluid containing low amount of starch. Further, the corn kernel mass in the most upstream screen unit S1 contains a higher amount of starch than the fraction f of the corn kernel mass in the most downstream screen unit S4.

One aim of using the fiber washing system described above, is to provide a contact time of at least 35 minutes, such as at least 40 minutes, at least 45 minutes, at least 50 minutes, at least 60 minutes, at least 70 minutes, at least 80 minutes, at least 90 minutes, at least 100 minutes, at least 110 minutes or at least 120 minutes, between corn kernel mass or fractions thereof and enzymes in the system, in order to increase the efficiency of the removal of the starch from fiber. The contact time/reaction time between enzymes and corn kernel mass or fractions thereof in the fiber washing system is also referred to as retention time. The contact time/reaction time between enzymes and corn kernel mass or fractions thereof in the space (V) is referred to as incubation time.

In one embodiment, the incubation time in said space (V) configured into the fiber washing system is at least 5 minutes such as at least 10 minutes, at least 15 minutes, at least 20 minutes, at least 30 minutes, at least 40 minutes, at least 45 minutes, at least 50 minutes, at least 60 minutes, at least 70 minutes, at least 80 minutes, at least 90 minutes, at least 100 minutes, at least 110 minutes or at least 120 minutes and less than 48 hours, such as less than 40 hours, less than 36 hours, less than 30 hours, less than 24 hours, less than 20 hours, less than 12 hours, less than 10 hours, less than 8 hours, less than 6 hours, less than 5 hours, less than 4 hours, less than 3 hours.

In one embodiment the incubation time in said space (V) is between 35 minutes and 48 hours such as between 35 minutes and 24 hours, 35 minutes and hours, 35 minutes and 6 hours, 35 minutes and 5 hours, 35 minutes and 4 hours, 35 minutes and 3 hours, 35 minutes and 2 hours, 45 minutes and 48 hours, 45 minutes and 24 hours, 45 minutes and 12 hours, 45 minutes and 6 hours, 45 minutes and 5 hours, 45 minutes and 4 hours, 45 minutes and 3 hours, 45 minutes and 2 hours 1-48 hours, 1-24 hours, 1-12 hours, 1-6 hours, 1-5 hours, 1-4 hours, 1-3 hours, 1-2 hours.

In one embodiment, the incubation temperature in said space (V) is between 25 and 95° C., such as between 25 and 90° C., 25 and 85° C., 25 and 80° C., 25 and 75° C., 25 and 70° C., 25 and 65° C., 25 and 60° C., 25 and 55° C., 25 and 53° C., 25 and 52° C., 30 and 90° C., 30 and 85° C., 30 and 80° C., 30 and 75° C., 30 and 70° C., 30 and 65° C., 30 and 60° C., 30 and 55° C., 30 and 53° C., 30 and 52° C., 35 and 90° C., 35 and 85° C., 35 and 80° C., 35 and 75° C., 35 and 70° C., 35 and 65° C., 35 and 60° C., 35 and 55° C., 35 and 53° C., 35 and 52° C., 39 and 90° C., 39 and 85° C., 39 and 80° C., 39 and 75° C., 39 and 70° C., 39 and 65° C., 39 and 60° C., 39 and 55° C., 39 and 53° C., 39 and 52° C.

It has been found advantageous to add enzymes at position being downstream of a most upstream screen unit S1 and upstream of a most downstream screen unit S4; in the embodiment of FIG. 1, the addition of enzymes is illustrated as being at the fluid position of the screen unit S3 (illustrated by the arrow in FIG. 1 labelled "Enzymes".

By adding the enzymes at an optimal point in the fiber washing system, the retention time can be prolonged, which may increase the efficiency of the removal or separation of starch from fiber. In order to provide a longer retention time than that provided by a typical mill, a space V (not shown in FIG. 1) may be arranged in the system and being fluidly connected to receive one of said first fractions s, one of said second fractions f, or a mixed first and second fraction s, f, preferably only a second fraction f, and configured to provide an incubation time for one or both fractions received in the space; and outletting the thereby incubated fraction or fractions to a downstream screen unit S4. It is noted that while it may be preferred to have a separate incubator unit arranged in the system, the flow lines connecting the screen units may also be used to provide the space.

According to embodiments wherein the fiber washing system comprises 2 screen units, dosing is preferred between the first and second screen unit or in a space configured between screen unit 1 and screen unit 2.

According to embodiments wherein the fiber washing system comprises 3 screen units, dosing is preferred in the second screen unit or in a space configured between screen unit 1 and screen unit 3, most preferred in screen unit 2, or a space configured between screen unit 2 and 3.

According to embodiments wherein the fiber washing system comprise 4 screen units, dosing is preferred in the second or third screen unit or in a space configured between screen unit 1 and screen unit 4, most preferred in screen unit 2, or a space configured between screen unit 2 and 3.

According to embodiments wherein the fiber washing system comprise 5 screen units, dosing is preferred in the second, third or fourth screen unit, or in a space configured between screen unit 1 and screen unit 5, most preferred in screen unit 3 or a space configured between screen unit 3 and 4.

According to embodiments wherein the fiber washing system comprise 6 screen units, dosing is preferred in the second, third, fourth or fifth screen unit, or in a space configured between screen unit 1 and screen unit 6, most preferred in screen unit 4, or a space configured between screen unit 4 and 5.

According to embodiments wherein the fiber washing system comprise 7 screen units, dosing is preferred in the second, third, fourth, fifth or sixth screen unit, or in a space configured between screen unit 1 and screen unit 7, most preferred in screen unit 4 or a space configured between screen unit 4 and 5.

According to embodiments wherein the fiber washing system comprise 8 screen units, dosing is preferred in the second, third, fourth, fifth, sixth and seventh screen unit, or in a space configured between screen unit 1 and screen unit 8, most preferred in screen unit 5 or a space configured between screen unit 5 and 6.

Thus, a system according to preferred embodiments of the invention is configured for
- inletting corn kernel mass and liquid to the most upstream screen unit S1, preferably by comprising an inlet into system feeding the matter to the most upstream screen unit S1;
- outletting the first fraction s1 from the most upstream screen unit S1 as a product stream containing starch, preferably by comprising an outlet from the most upstream screen unit feeding a fibreless stream out from the system;
- inletting process water, preferably arranged for inletting process water to a most downstream screen unit S4; the inlet of process water is preferably an inlet to the most downstream screen unit S4;
- outletting the second fraction f4 from most downstream screen unit S4 as a washed corn kernel mass containing a lower amount of starch and gluten than the original corn kernel mass; preferably by comprising an outlet from the most downstream screen unit.

The system is also configured for introducing hydrolytic enzymes into the system, which may be an inlet arranged at a preferred position to allow contact between the corn kernel mass or fractions thereof and the one or more hydrolytic enzymes.

Figure 2:
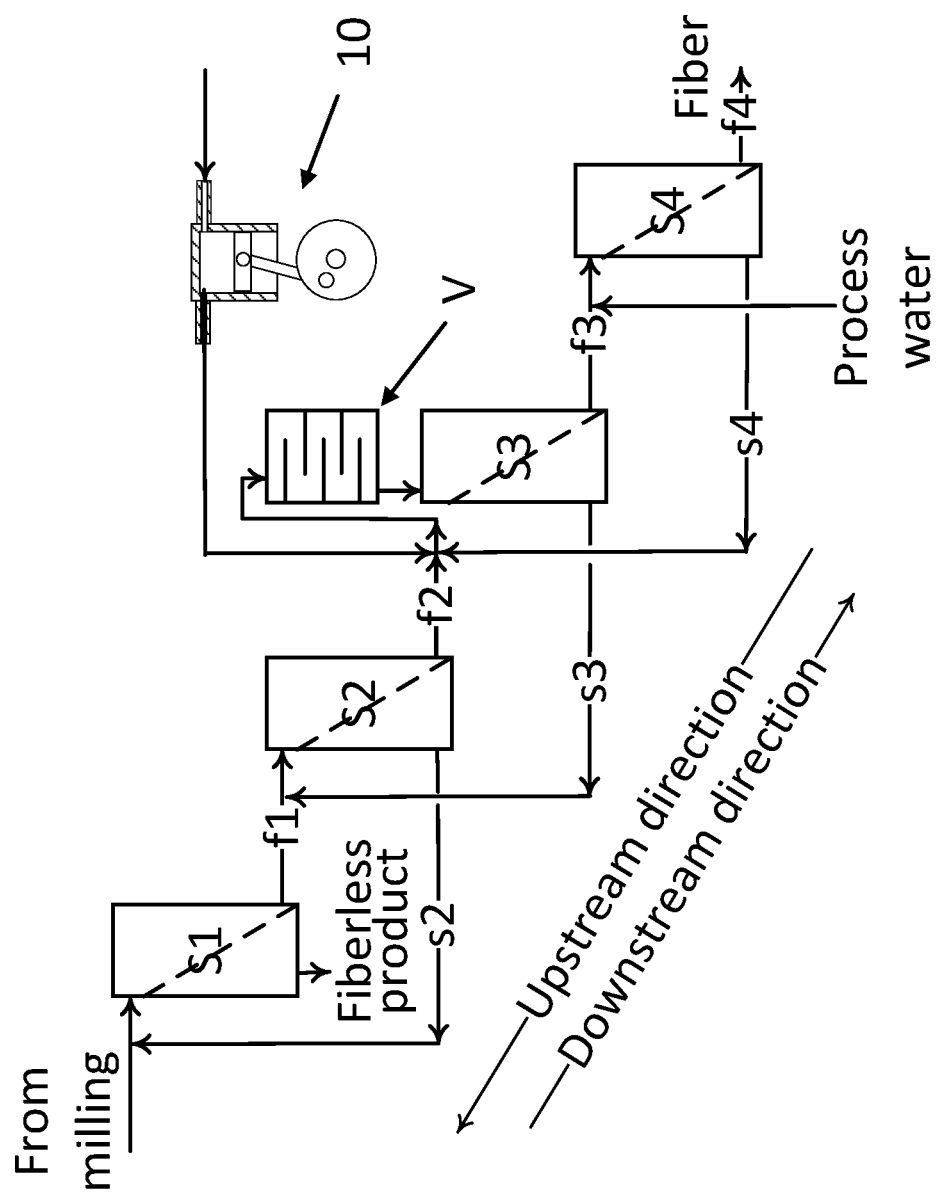

Reference is made to FIG. 2 schematically illustrating a further embodiment of a system according to the present invention. The same notation as used in FIG. 1 is used in FIG. 2. As presented in FIG. 2, the screen units S1 to S4 all comprises a screening element (screen) indicated by a slanted, dotted line inside the screen units. This slanted dotted line illustrate a device configured for separating out a fraction f containing fiber and a fraction preferably not containing any fiber; this could for instance be provided by a band filter or a filter in general arranged inside wall parts defining an interior void of a screen unit.

In the embodiment shown in FIG. 2, the various fraction to be mixed are illustrated as being mixed outside the screen units S1-S4. However, they may be mixed inside the screen units.

As also illustrated in FIG. 2, the space V is a separate container being fluidly connected to the screen unit S3 so that the screen unit S3 receives fluid with fiber and enzymes after the fluid with fiber and enzymes has had an incubation time in the space V. As schematically illustrated in FIG. 2, the space V may have baffle plates for assuring the fluid does not flow in a straight line from inlet to outlet of the container, which could otherwise short-cut the flow to provide an incubation time.

FIG. 2 also illustrates that enzymes are applied to the streams f2 and s4 going into the space V. In the embodiment shown, the enzymes are dosed by a dosing pump 10 illustrated schematically be a piston pump driven by a crank shaft where the amount of enzymes dosed is controlled by the rotation of the crank shaft (one-way inlet and outlet valves are present in the cylinder or cylinder head but not illustrated).

Thus, a system according to the present invention is preferably configured for introducing hydrolytic enzymes into said first fraction (s), and/or into said second fraction (f), and/or into a mixed first and second fraction and/or into the stream of process water supplied to the system.

The number of screen units S may be selected according to e.g. the volumetric capacity to separate into two stream and/or the other design aims. However, a system according to present invention will in general have a most upstream screen unit, a most downstream screen unit and preferably one or more intermediate screen units fluidic arranged in between the most upstream and most downstream screen units. That is, with reference to FIGS. 1 and 2, a preferred system will comprise a most upstream screen unit S1 and a most downstream screen unit S4 and a number of screen units (e.g. 2) arranged in between, where arranged in between refers to being fluidly connected as illustrated in the FIGS. 1 and 2.

In detail, the fluidly connected counter current washing configuration, as disclosed in FIGS. 1 and 2, typically comprising the plurality of screen units S1 . . . S4 being arranged in a manner so:

a second fraction f1 produced by an upstream screen unit S1 is mixed with a first fraction s3 produced by a downstream screen unit S3, and said mixed fractions being separated by a screen unit S2, being intermediate between said upstream and said downstream screen units S1, S3, into a first fraction s2 and a second fraction f2.

While this disclosure is made with reference to screen unit S3, the same description may apply for any intermediate screen units, such as screen S2, or other intermediate screen units where intermediate screen unit refers to a screen unit being arranged downstream of the most upstream screen unit and upstream of a most downstream screen unit.

As illustrated in FIG. 2, it is in some embodiments preferred that mixing of a second fraction f1 and a first fraction s3 occurs prior to being inlet into an intermediate screen unit S2. Such a mixing may be provided by inletting the two fractions into a mixing chamber comprising stirring means providing typically a vigorous agitation of the fluid or the mixing may be provide by a manifold having an inlet for each stream and an outlet for the mixed stream.

As an alternative to mixing prior to be inlet into a screen unit, mixing of a second fraction f1 and a first fractions 3 may occur inside an intermediate screen unit S2. This may for instance be accomplished by the interior of the screen unit being equipped with a stirring means providing typically a vigorous agitation of the fluid inside the screen unit.

Although the embodiments disclosed in FIGS. 1 and 2 are shown to comprise more than two screen units, a system is considered to be fully operational with as little as two screen units. Thus, it is generally preferred that the system comprising 2-8 screen units typically arranged as illustrated in FIG. 1 or 2.

Further, the dimension of the space (in m$^3$) is preferably configured to provide an incubation time of at least at least 5 minutes, such as at least 10 minutes, at least 15 minutes, at least 20 minutes at least 25 minutes, at least 30 minutes, at least 35 minutes, at least 40 minutes, at least 45 minutes, at least 50 minutes, at least 55 minutes, at least 60 minutes, at least 70 minutes, at least 80 minutes, at least 90 minutes, at least 100 minutes, at least 110 minutes, at least 120 minutes. The space (V) designated for incubation preferably has a volume of at least 30 m$^3$, at least 40 m$^3$, at least 50 m$^3$, at least 60 m$^3$, at least 70, m$^3$, at least 80, m$^3$, at least 90, m$^3$, at least 100 m$^3$, at least 110 m$^3$, at least 120 m$^3$, at least 130 m$^3$, at least 140 m$^3$, at least 150 m$^3$, at least 160 m$^3$, at least 170 m$^3$, at least 180 m$^3$, at least 190 m$^3$, at least 200 m$^3$, at least 210 m$^3$, at least 220 m$^3$, at least 230 m$^3$, at least 240 m$^3$, at least 250 m$^3$, at least 260 m$^3$, at least 270 m$^3$, at least 280 m$^3$, at least 290 m$^3$, at least 300 m$^3$, at least 400 m$^3$, or at least 500 m$^3$. The incubation time may also be in more than one space V with a total or combined volume of at least 100 m$^3$, at least 110 m$^3$, at least 120 m$^3$, at least 130 m$^3$, at least 140 m$^3$, at least 150 m$^3$, at least 160 m$^3$, at least 170 m$^3$, at least 180 m$^3$, at least 190 m$^3$, at least 200 m$^3$, at least 210 m$^3$, at least 220 m$^3$, at least 230 m$^3$, at least 240 m$^3$, at least 250 m$^3$, at least 260 m$^3$, at least 270 m$^3$, at least 280 m$^3$, at least 290 m$^3$, at least 300 m$^3$, at least 400 m$^3$, at least 500 m$^3$.

During the incubation time, it is preferred that the fluid received in the space V is not screened. Thus, the fluid leaving the space V has the same composition, e.g. of starch and fiber, as the fluid received in the space V, although it preferably contains a higher proportion of starch that has been released from the fibers.

To assure intimate contact between the enzymes and the fiber, it may be preferred to configure the space V for agitation of matter contained in said space V, such as by comprising a rotor or impeller.

As illustrated in FIG. 2, it is preferred to arrange the space V downstream of the most upstream screen unit S1 and upstream of said most downstream screen unit S4; in particular, the embodiment of FIG. 2 illustrates that the space V is arranged to feed fluid into the second most downstream screen unit S3.

As disclosed herein, the space may be provided in different manner and as illustrated in FIG. 2 the space V may preferably be provided as a separate incubator unit. The incubator unit may be configured by suitable fluid lines to receive a first fraction s, a second fraction f or a combination of a first and a second fraction s,f, preferably only a second fraction f, and deliver the thereby incubated material to a downstream screen unit S3.

Figure 3:
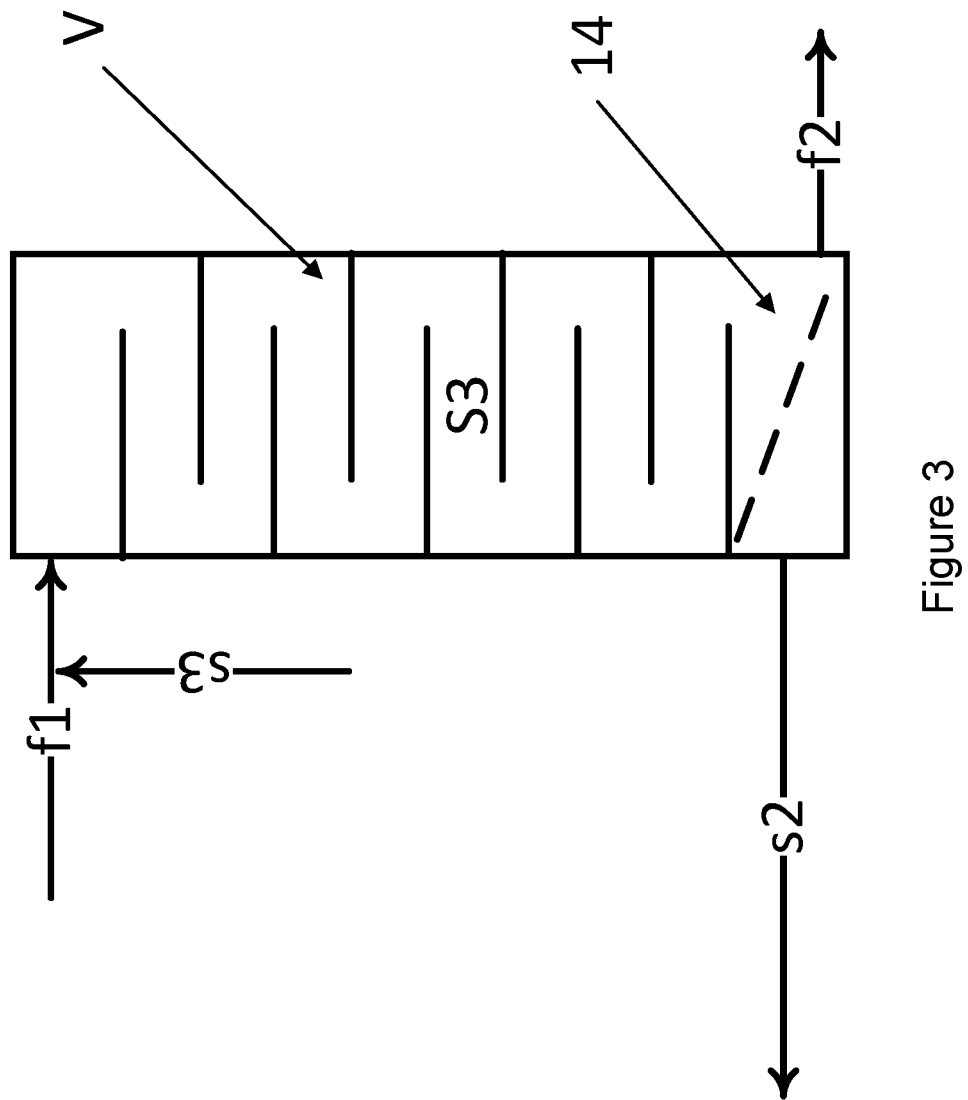
FIG. 3 schematically illustrates a screen unit with an built-in incubator.

Reference is made to FIG. 3 schematically illustrating a screen unit with an build-in incubator/space V. As illustrated the screen unit/incubator comprising at the lower end, a screening element 14 and above that a space V. Inside the space baffle plates are arranged to avoid short-cut in the fluid flow from the upper end (receiving in the disclosed embodiment of FIG. 3 fractions f1 and s3) towards the screening element 14. As also illustrated, the fiberless stream s2 is screened out providing a fiber containing fraction f2.

The enzyme used in releasing the starch from the corn kernel mass typically has a thermal window inside which the release of enzyme is most efficient and it may therefore be advantageous to be able to control the temperature at selected positions in the system, such as in the space V. To this, a system according to the present invention may preferably comprising thermo elements for providing an incubation temperature of the fluid inside said space (V), preferably in the range 35-70° C., such as in the range of 40-60° C., such as in the range of 39-53° C., such as in the range of 45-53° C., such as in the range of 39-48° C., such as 47° C. In the embodiment where the space is provided as a separate incubation unit (as in FIG. 2) the thermo elements may be arranged inside the incubation unit and/or on a shell defining the enclosure of the incubation unit.

The thermo elements are preferably thermostat-able heating/cooling elements being adapted to measure the temperature and change the heat flux into/out from the space to control the temperature of material contained in the space to be within a predefined range.

In some preferred embodiments, the thermostat-able heating elements comprising electrical heating/cooling elements or liquid heating/cooling elements and temperature sensors.

As presented herein, the screen unit provides a separation of fluid into two fractions s and f and the screen unit typically screens in a mechanical manner where one or more, such as all the screen units, comprises one or more screening element having openings (as illustrated e.g. in FIG. 2 with a slanted, dotted lines) configured for allowing passage of solid matter below a predefined size. The predefined size may be defined according to a number of design criteria. However, it typically preferred than no fiber is allowed to pass through the opening. On the other hand to small opening may have a tendency to become blocked and in many instances the actual size of openings is selected by taking the blocking aspect and the screening aspect into consideration, which may result in that smaller amounts of fibers are allowed to pass through.

Figure 4:
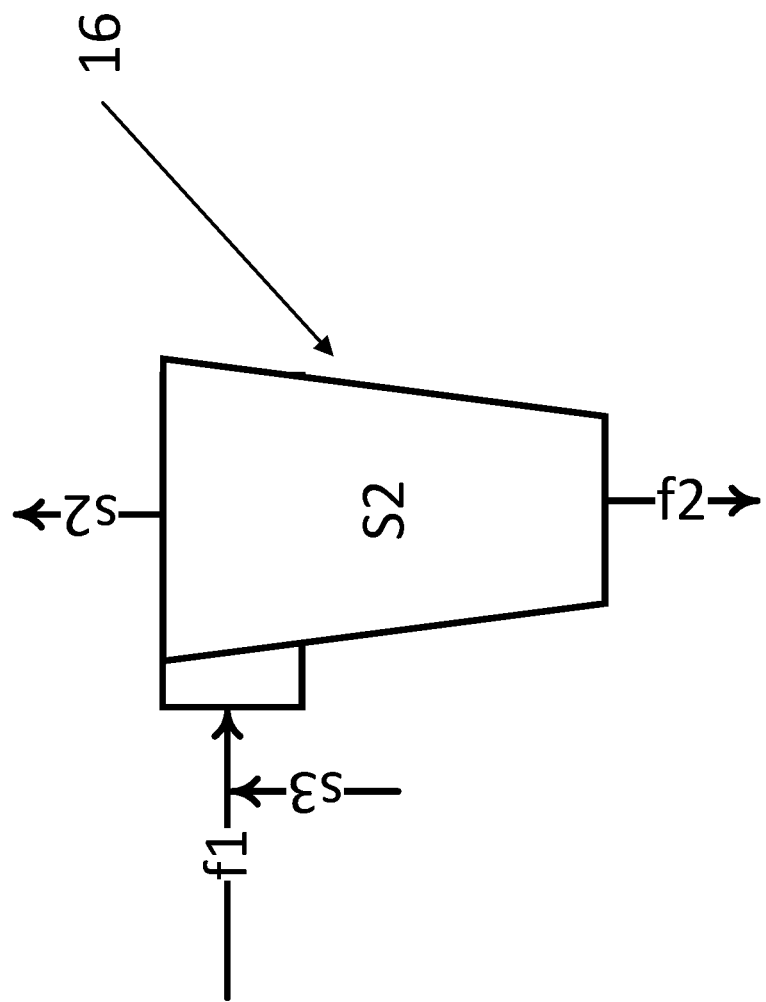
FIG. 4 schematically illustrates a screen unit in the form of a hydro-cyclone.

In some preferred embodiments, one or more such as all screen units comprises rotor blade and/or sieves configured for providing said two fractions s, f. As an alternative to screening elements made up by openings one or more such as all screen units may be hydro-cyclones 16 as illustrated schematically in FIG. 4.

As disclosed above, the system is configured to introduce hydrolytic enzymes into said first fraction s and/or into said second fraction f and/or into a mixed first and second fraction and/or into the process water, by means of a dosing device—see FIG. 2.

Such a dosing device is typically adapted to provide a controllable dosing quantity of enzymes, preferably according to a predetermined specific ratio between amount of enzymes and infeed of corn kernel mass to the system. To accomplish this, the dosing device 10 could be a metering pump as illustrated by a piston pump in FIG. 2.

Alternatively, the dosing device may be a gravity flow dispenser having a controllable outflow valve configured for controlling the amount of enzyme flowing through the flow valve.

In one embodiment, the GH5 polypeptide of the present invention has xylanase activity. In one embodiment, the GH30 polypeptide of the present invention has xylanase activity. In one embodiment the GH5 polypeptide of the present invention has an amount of xylanase activity which is sufficient to release an amount of starch and gluten which is at least 15% (w/w) of fiber dry matter, such as at least 16%, 17%, 18%, 19%, 20% 21% or at least 22% (w/w) of fiber dry matter, in a procedure comprising the steps of:

i. Providing a sample of pressed fiber from a corn wet-mill plant;
ii. Re-suspending the sample in buffer (pH 4, 0.02M Na Acetate) to provide a slurry containing 5% dry solids.
iii. Adding GH5 polypeptide to the slurry in amounts corresponding to 35 μg enzyme protein (EP) per g dry-solids substrate, such as 70 μg enzyme protein (EP) per g dry-solids substrate, in combination with cellulolytic enzymes at an amount corresponding to 280 μg enzyme protein (EP) per g dry-solids substrate;
iv. Incubation of sample at a temperature of 40 or 52° C. in an air-heated incubator with constant shaking for 120 minutes.
v. Quick cooling of sample in ice-water (5° C.) before processing
vi. Transferring of slurry to a 150-micron sieve and collection of filtrate passing through.
vii. Pressing of retaining fiber on sieve and collection of filtrate passing through, combining the collected filtrate with the first filtrate.
viii. Transferring of pressed fiber to a 200 ml water containing beaker and stirring of the mixture.
ix. Transferring the slurry to a 150-micron sieve and collection of filtrate passing through, combining the collected filtrate with the first filtrate.
x. Pressing of retaining fiber on sieve and collection of filtrate passing through, combining the collected filtrate with the first filtrate.
xi. Repetition of step viii to x one more time.
xii. Vacuum filtration of combined filtrate through a glass micro filter paper (WHATMAN) which retains the insoluble solids that were released from the fiber passed through the 150 micron sieve.
xiii. Passing 200 ml water over the filter paper to remove any trace solubles
xiv. Drying and weighing of the total insoluble solids retained on the filter paper, reported as starch and gluten released (w/w) of fiber dry matter.

In one embodiment, the GH5 polypeptide of the present invention further comprises one or more of the following activities: endo-β-1,4-glucanase/cellulase (EC 3.2.1.4) activity, endo-β-1,4-xylanase (EC 3.2.1.8) activity, β-glucosidase (EC 3.2.1.21) activity, β-mannosidase (EC 3.2.1.25) activity, β-glucosylceramidase (EC 3.2.1.45) activity, glucan β-1,3-glucosidase (EC 3.2.1.58) activity, licheninase (EC 3.2.1.73) activity, exo-β-1,4-glucanase/cellodextrinase (EC 3.2.1.74) activity and/or glucan endo-1,6-β-glucosidase (EC 3.2.1.75) activity, mannan endo-β-1,4-mannosidase (EC 3.2.1.78) activity, cellulose β-1,4-cellobiosidase (EC 3.2.1.91) activity, steryl β-glucosidase (EC 3.2.1.104) activity, endoglycoceramidase (EC 3.2.1.123) activity, chitosanase (EC 3.2.1.132) activity, β-primeverosidase (EC 3.2.1.149) activity, xyloglucan-specific endo-β-1,4-glucanase (EC 3.2.1.151) activity, endo-β-1,6-galactanase (EC 3.2.1.164) activity, hesperidin 6-O-α-L-rhamnosyl-β-glucosidase (EC 3.2.1.168) activity, β-1,3-mannanase (EC 3.2.1.-) activity and arabinoxylan-specific endo-β-1,4-xylanase (EC 3.2.1.-) activity and mannan transglycosylase (EC 2.4.1.-) activity.

In one embodiment, the GH30 polypeptide of the present invention further comprise one or more of the following activities: endo-β-1,4-xylanase (EC 3.2.1.8) activity, β-glucosidase (EC 3.2.1.21) activity, β-glucuronidase (EC 3.2.1.31) activity, β-xylosidase (EC 3.2.1.37) activity, β-fucosidase (EC 3.2.1.38) activity, glucosylceramidase (EC 3.2.1.45) activity, β-1,6-glucanase (EC 3.2.1.75) activity, glucuronoarabinoxylan endo-β-1,4-xylanase (EC 3.2.1.136) activity, endo-β-1,6-galactanase (EC:3.2.1.164) activity, and [reducing end] β-xylosidase (EC 3.2.1.-) activity.

In one embodiment, the GH5 polypeptide of the present invention, is selected from a group consisting of:
i) A mature polypeptide of the amino acid sequence set forth in any one of SEQ ID NO: 1-3; SEQ ID NO: 8, SEQ ID NO: 10 or SEQ ID NO: 12;
ii) A mature polypeptide, which has at least 60% sequence identity to the mature polypeptide in i), such as at least 65%, 70%, 75%, 80%, 85%, 90%, 95%, 96%, 97%, 98%, 99% or 100% sequence identity.
iii) A subsequence of any one of the mature polypeptides in i) and ii); preferably the subsequence has xylanase activity.

In one embodiment, the GH30 polypeptide of the present invention, is selected from a group consisting of:
i) A mature polypeptide of the amino acid sequence set forth in SEQ ID NO: 4; SEQ ID NO:5; SEQ ID NO:6 or SEQ ID NO:7;
ii) A mature polypeptide, which has at least 60% sequence identity to the mature polypeptide in i), such as at least 65%, 70%, 75%, 80%, 85%, 90%, 95%, 96%, 97%, 98%, 99% or 100% sequence identity.
iii) A subsequence of any one of the mature polypeptides in i) and ii); preferably the subsequence has xylanase activity.

The term "mature polypeptide" means a polypeptide in its final form following translation and any post-translational modifications, such as N-terminal processing, C-terminal truncation, glycosylation, phosphorylation, etc.

In one embodiment, the mature polypeptide of SEQ ID NO: 1 comprises/consists/consists essentially of amino acids 1 to 655. In another embodiment, the mature polypeptide of SEQ ID NO: 1 comprises/consists/consists essentially of amino acids 28 to 655 of SEQ ID NO: 1, amino acids 1 to 27 of SEQ ID NO: 1 being a signal peptide. In another embodiment, the mature polypeptide of SEQ ID NO: 1 comprises/consists/consists essentially of amino acids 36 to 655 of SEQ ID NO: 1, amino acids 28 to 35 of SEQ ID NO: 1 being a his-tag. In another embodiment, the mature polypeptide of SEQ ID NO: 1 comprises/consists/consists essentially of at least amino acids 37 to 655 of SEQ ID NO: 1. In another embodiment, the mature polypeptide of SEQ ID NO: 1 comprises/consists/consists essentially of at least amino acids 40 to 655 of SEQ ID NO: 1. In another embodiment, the mature polypeptide of SEQ ID NO: 1 comprises/consists/consists essentially of at least amino acids 45 to 655 of SEQ ID NO: 1.

In one embodiment, the mature polypeptide of SEQ ID NO: 2 comprises/consists/consists essentially of amino acids 1 to 555 of SEQ ID NO: 2. In another embodiment, the mature polypeptide of SEQ ID NO: 2 comprises/consists/consists essentially of amino acids 7 to 555 of SEQ ID NO: 2, amino acids 1 to 6 of SEQ ID NO: 2 being a his-tag. In another embodiment, the mature polypeptide of SEQ ID NO: 2 comprises/consists/consists essentially of amino acids 10 to 555 of SEQ ID NO: 2. In another embodiment, the mature polypeptide of SEQ ID NO: 2 comprises/consists/consists essentially of amino acids 15 to 555 of SEQ ID NO: 2. In another embodiment, the mature polypeptide of SEQ ID NO: 2 comprises/consists/consists essentially of amino acids 20 to 555 of SEQ ID NO: 2. In another embodiment, the mature polypeptide of SEQ ID NO: 2 comprises/consists/consists essentially of amino acids 30 to 555 of SEQ ID NO: 2.

In one embodiment, the mature polypeptide of SEQ ID NO: 3 comprises/consists/consists essentially of amino acids 1 to 585 of SEQ ID NO: 3. In another embodiment, the mature polypeptide of SEQ ID NO: 3 comprises/consists/consists essentially of amino acids 28 to 585 of SEQ ID NO: 3, amino acids 1 to 27 of SEQ ID NO: 3 being a signal peptide. In another embodiment, the mature polypeptide of SEQ ID NO: 3 comprises/consists/consists essentially of amino acids 36 to 585 of SEQ ID NO: 3, amino acids 28 to 35 of SEQ ID NO: 3 being a his-tag. In another embodiment, the mature polypeptide of SEQ ID NO: 3 comprises/consists/consists essentially of at least amino acids 37 to 585 of SEQ ID NO: 3. In another embodiment, the mature polypeptide of SEQ ID NO: 3 comprises/consists/consists essentially of at least amino acids 40 to 585 of SEQ ID NO: 3. In another embodiment, the mature polypeptide of SEQ ID NO: 3 comprises/consists/consists essentially of at least amino acids 45 to 585 of SEQ ID NO: 3.

In one embodiment, the mature polypeptide of SEQ ID NO: 4 comprises/consists/consists essentially of amino acids 1 to 391 of SEQ ID NO: 4. In another embodiment, the mature polypeptide of SEQ ID NO: 4 comprises/consists/consists essentially of amino acids 5 to 391 of SEQ ID NO: 4. In another embodiment, the mature polypeptide of SEQ ID NO: 4 comprises/consists/consists essentially of amino acids 10 to 391 of SEQ ID NO: 4. In another embodiment, the mature polypeptide of SEQ ID NO: 4 comprises/consists/consists essentially of amino acids 15 to 391 of SEQ ID NO: 4. In another embodiment, the mature polypeptide of SEQ ID NO: 4 comprises/consists/consists essentially of amino acids 20 to 391 of SEQ ID NO: 4. In another embodiment, the mature polypeptide of SEQ ID NO: 4 comprises/consists/consists essentially of amino acids 30 to 391 of SEQ ID NO: 4.

In one embodiment, the mature polypeptide of SEQ ID NO: 5 comprises/consists/consists essentially of amino acids 1 to 417 of SEQ ID NO: 5. In another embodiment, the mature polypeptide of SEQ ID NO: 5 comprises/consists/consists essentially of amino acids 27 to 417 of SEQ ID NO: 5, amino acids 1 to 26 of SEQ ID NO: 5 being a signal peptide.

In one embodiment, the mature polypeptide of SEQ ID NO: 6 comprises/consists/consists essentially of amino acids 1 to 417 of SEQ ID NO: 6. In another embodiment, the mature polypeptide of SEQ ID NO: 6 comprises/consists/consists essentially of amino acids 27 to 417 of SEQ ID NO: 6, amino acids 1 to 26 of SEQ ID NO: 6 being a signal peptide.

In one embodiment, the mature polypeptide of SEQ ID NO: 7 comprises/consists/consists essentially of amino acids 1 to 417 of SEQ ID NO: 7. In another embodiment, the mature polypeptide of SEQ ID NO: 7 comprises/consists/consists essentially of amino acids 27 to 417 of SEQ ID NO: 7, amino acids 1 to 26 of SEQ ID NO: 7 being a signal peptide.

In one embodiment, the mature polypeptide of SEQ ID NO: 8 comprises/consists/consists essentially of amino acids 1 to 557. In another embodiment, the mature polypeptide of SEQ ID NO: 8 comprises/consists/consists essentially of amino acids 8 to 557 of SEQ ID NO: 8, amino acids 1 to 7 of SEQ ID NO: 8 being a his-tag. In another embodiment, the mature polypeptide of SEQ ID NO: 8 comprises/consists/consists essentially of at least amino acids 28 to 557 of SEQ ID NO: 8.

In one embodiment, the mature polypeptide of SEQ ID NO: 10 comprises/consists/consists essentially of amino acids 1 to 576 of SEQ ID NO: 10. In another embodiment, the mature polypeptide of SEQ ID NO: 10 comprises/consists/consists essentially of amino acids 24 to 576 of SEQ ID NO: 10, amino acids 1 to 23 of SEQ ID NO: 10 being a signal peptide.

In one embodiment, the mature polypeptide of SEQ ID NO: 12 comprises/consists/consists essentially of amino acids 1 to 565 of SEQ ID NO: 12.

In the context of the present invention, the term "subsequence" means a polypeptide in which one or more (e.g., several) amino acid residues are absent from the amino (N-) terminus and/or from the carboxy (C-) terminus of a mature polypeptide; wherein the subsequence has xylanase activity. In some embodiments, the number of amino acid residues which are absent in a "subsequence" is at the most 20, such as at the most 19, 18, 17, 16, 15, 14, 13, 12, 11, 10, 9, 8, 7, 6, 5, 4, 3, 2 or at the most 1 amino acid residue.

In some embodiment, a subsequence of any one of the mature polypeptides may be at least 150 amino acids in length or at least 200 amino acids in length or at least 250 amino acids in length or at least 300 amino acids in length or at least 350 amino acids in length or at least 400 amino acids in length or at least 450 amino acids in length or at least 500 amino acids in length or at least 550 amino acids in length or at least 600 amino acids in length or at least 650 amino acids in length.

In one embodiment, a subsequence of SEQ ID NO: 1 of the mature polypeptides may be at least 200 amino acids in length or at least 250 amino acids in length or at least 300 amino acids in length or at least 350 amino acids in length or at least 400 amino acids in length or at least 450 amino acids in length or at least 500 amino acids in length or at least 550 amino acids in length or at least 600 amino acids in length or at least 650 amino acids in length.

In one embodiment, a subsequence of SEQ ID NO: 2 of the mature polypeptides may be at least 200 amino acids in length or at least 250 amino acids in length or at least 300 amino acids in length or at least 350 amino acids in length or at least 400 amino acids in length or at least 450 amino acids in length or at least 500 amino acids in length or at least 550 amino acids in length.

In one embodiment, a subsequence of SEQ ID NO: 3 of the mature polypeptides may be at least 200 amino acids in length or at least 250 amino acids in length or at least 300 amino acids in length or at least 350 amino acids in length or at least 400 amino acids in length or at least 450 amino acids in length or at least 500 amino acids in length or at least 550 amino acids in length or at least 560 amino acids in length or at least 570 amino acids in length or at least 580 amino acids in length.

In one embodiment, a subsequence of SEQ ID NO: 4 of the mature polypeptides may be at least 150 amino acids in length or at least 200 amino acids in length or at least 250 amino acids in length or at least 300 amino acids in length or at least 350 amino acids in length or at least 360 amino acids in length or at least 370 amino acids in length or at least 380 amino acids in length or at least 390 amino acids in length.

In one embodiment, a subsequence of SEQ ID NO: 5 of the mature polypeptides may be at least 150 amino acids in length or at least 200 amino acids in length or at least 250 amino acids in length or at least 300 amino acids in length or at least 350 amino acids in length or at least 360 amino acids in length or at least 370 amino acids in length or at least 380 amino acids in length or at least 390 amino acids in length.

In one embodiment, a subsequence of SEQ ID NO: 6 of the mature polypeptides may be at least 150 amino acids in length or at least 200 amino acids in length or at least 250 amino acids in length or at least 300 amino acids in length or at least 350 amino acids in length or at least 360 amino acids in length or at least 370 amino acids in length or at least 380 amino acids in length or at least 390 amino acids in length.

In one embodiment, a subsequence of SEQ ID NO: 7 of the mature polypeptides may be at least 150 amino acids in length or at least 200 amino acids in length or at least 250 amino acids in length or at least 300 amino acids in length or at least 350 amino acids in length or at least 360 amino acids in length or at least 370 amino acids in length or at least 380 amino acids in length or at least 390 amino acids in length.

In one embodiment, a subsequence of SEQ ID NO: 8 of the mature polypeptides may be at least 200 amino acids in length or at least 250 amino acids in length or at least 300 amino acids in length or at least 350 amino acids in length or at least 400 amino acids in length or at least 450 amino acids in length or at least 500 amino acids in length or at least 550 amino acids in length or at least 600 amino acids in length or at least 650 amino acids in length. In one embodiment, a subsequence of SEQ ID NO: 10 of the mature polypeptides may be at least 200 amino acids in length or at least 250 amino acids in length or at least 300 amino acids in length or at least 350 amino acids in length or at least 400 amino acids in length or at least 450 amino acids in length or at least 500 amino acids in length or at least 550 amino acids in length or at least 600 amino acids in length or at least 650 amino acids in length. In one embodiment, a subsequence of SEQ ID NO: 12 of the mature polypeptides may be at least 200 amino acids in length or at least 250 amino acids in length or at least 300 amino acids in length or at least 350 amino acids in length or at least 400 amino acids in length or at least 450 amino acids in length or at least 500 amino acids in length or at least 550 amino acids in length or at least 600 amino acids in length or at least 650 amino acids in length.

In one embodiment, the enzyme composition comprising one or more hydrolytic enzymes further comprise one or more enzymes selected form the group consisting of: cellulases (EC 3.2.1.4), xylanases (EC 3.2.1.8) arabinofuranosidases (EC 3.2.1.55 (Non-reducing end alpha-L-arabinofuranosidases); EC 3.2.1.185 (Non-reducing end beta-L-arabinofuranosidases) cellobiohydrolase I (EC 3.2.1.150), cellobiohydrolase II (E.C. 3.2.1.91), cellobiosidase (E.C. 3.2.1.176), beta-glucosidase (E.C. 3.2.1.21), beta-xylosidases (EC 3.2.1.37) and proteases (E.C 3.4).

In one embodiment, the one or more hydrolytic enzymes is expressed in an organism with a cellulase background, such as *Trichoderma reesei*. According to these embodiments the GH5 and/or the GH30 polypeptides defined according to the invention is/are expressed together with endogenous cellulases from *Trichoderma*.

In one embodiment, the enzyme composition comprising one or more hydrolytic enzymes may comprise cellulases expressed in *Trichoderma reesei* and other hydrolytic enzymes which are added to the enzyme composition in a purified or semi-purified form.

In one embodiment, the one or more hydrolytic enzymes are purified. The purified enzymes may be used in an enzyme composition as described in other embodiments of the present invention.

In one embodiment, the one or more hydrolytic enzymes is/are in a liquid composition. The composition may be homogenous or heterogeneous.

In one embodiment, the one or more hydrolytic enzymes is/are in a solid composition.

In one embodiment, the effective amount of one or more hydrolytic enzymes admixed with one or more fractions of said corn kernel mass, is between 0.005-0.5 kg enzyme protein (EP)/metric tonne (MT) corn kernels entering the wet milling process, such as between 0.010-0.5 kg EP/MT corn kernel, such as between 0.05-0.5 kg/MT corn kernel or 0.075-0.5 kg/MT or 0.1-0.5 kg/MT corn kernel or 0.005-0.4 kg/MT corn kernel or 0.01-0.4 kg/MT corn kernel or 0.05-0.4 kg/MT corn kernel or 0.075-0.4 kg/MT corn kernel or 0.1-0.4 kg/MT corn kernel or 0.005-0.3 kg/MT corn kernel or 0.01-0.3 kg/MT corn kernel or 0.05-0.3 kg/MT corn kernel or 0.075-0.3 kg/MT or 0.1-0.3 kg/MT corn kernel or 0.005-0.2 kg/MT corn kernel or 0.010-0.2 kg/MT corn kernel or 0.05-0.2 kg/MT corn kernel or 0.075-0.2 kg/MT or 0.1-0.2 kg/MT corn kernel or such as 0.075-0.10 kg/MT corn kernel or 0.075-0.11 kg/MT corn kernel.

Enzymatic treatment of corn kernels or a fraction of corn kernels with a hydrolytic enzyme composition, comprising at least one GH5 polypeptide or at least one GH30 polypeptide or a combination of at least one GH5 and at least one GH30 polypeptide, provide corn starch, corn gluten and corn fiber products, that differ from products produced by other methods known in the art.

In one aspect, the present invention relates to a composition comprising corn starch, said composition being obtainable by the method of the invention.

In one aspect, the present invention relates to a composition comprising corn gluten, said composition being obtainable by the method of the invention.

In one aspect, the present invention relates to a composition comprising corn fiber, said composition being obtainable by the method of the invention.

In one aspect, the present invention relates to an enzyme composition comprising an isolated GH30 polypeptide as defined herein.

In one aspect, the present invention relates to an enzyme composition comprising an isolated GH5 polypeptide as defined herein.

In one aspect, the present invention relates to an enzyme composition comprising an isolated GH30 polypeptide as defined herein and an isolated GH5 polypeptide as defined herein.

In one embodiment, the enzyme composition according to the invention, wherein at least one of said hydrolytic enzymes is selected from the group consisting of a GH30 polypeptide, a GH5 polypeptide or a combination thereof, further comprises one or more enzymes selected from the group consisting of cellulases (EC 3.2.1.4), xylanases (EC 3.2.1.8) arabinofuranosidases (EC 3.2.1.55 (Non-reducing end alpha-L-arabinofuranosidases); EC 3.2.1.185 (Non-reducing end beta-L-arabinofuranosidases) cellobiohydrolase I (EC 3.2.1.150), cellobiohydrolase II (E.C. 3.2.1.91), cellobiosidase (E.C. 3.2.1.176), beta-glucosidase (E.C. 3.2.1.21), beta-xylosidases (EC 3.2.1.37) or proteases (E.C 3.4).

In preferred embodiments the enzyme composition comprises cellulase obtained from a culture of *Trichoderma reesei*, such as a culture of *Trichoderma reesei* ATCC 26921. Suitable cellulases are available; e.g. from NOVOZYMES A/S under the commercial name CELLUCLAST®.

A further aspect of the invention relates to the use of a GH30 polypeptide in corn wet milling.

The GH30 polypeptide may in particular be a polypeptide as defined herein above. Preferably, the corn wet milling is performed using a wet milling process as defined above.

In another aspect, the invention provides the use of a GH5 polypeptide in corn wet milling. The GH5 polypeptide may in particular be a polypeptide as defined herein above. Preferably, the corn wet milling is performed using a wet milling process as defined in any above.

Yet another aspect of the invention provides the use of an enzyme composition as described defined above in corn wet milling, preferably in a corn wet milling process as defined above.

Preferably, the GH30 polypeptide, the GH5 polypeptide and/or the enzyme composition, when used according to the invention is used for the purpose of increasing the total starch yield and/or gluten yield from corn kernels in a wet milling process.

Polypeptides Having Xylanase Activity

In an embodiment, the present invention relates to isolated polypeptides having a sequence identity to the mature polypeptide of SEQ ID NO: 10 of at least 80%, at least 85%, at least 90%, at least 91%, at least 92%, at least 93%, at least 94%, at least 95%, at least 96%, at least 97%, at least 98%, at least 99%, or 100%, which have xylanase activity. In one aspect, the polypeptides differ by up to 10 amino acids, e.g., 1, 2, 3, 4, 5, 6, 7, 8, 9, or 10, from the mature polypeptide of SEQ ID NO: 10.

A polypeptide of the present invention preferably comprises or consists of the amino acid sequence of SEQ ID NO: 10 or an allelic variant thereof; or is a fragment thereof having xylanase activity. In another aspect, the polypeptide comprises or consists of the mature polypeptide of SEQ ID NO: 10. In another aspect, the polypeptide comprises or consists of amino acids 24 to 576 of SEQ ID NO: 10.

In an embodiment, the present invention relates to isolated polypeptides having a sequence identity to the mature polypeptide of SEQ ID NO: 12 of at least 80%, at least 85%, at least 90%, at least 91%, at least 92%, at least 93%, at least 94%, at least 95%, at least 96%, at least 97%, at least 98%, at least 99%, or 100%, which have xylanase activity. In one aspect, the polypeptides differ by up to 10 amino acids, e.g., 1, 2, 3, 4, 5, 6, 7, 8, 9, or 10, from the mature polypeptide of SEQ ID NO: 12.

A polypeptide of the present invention preferably comprises or consists of the amino acid sequence of SEQ ID NO: 12 or an allelic variant thereof; or is a fragment thereof having xylanase activity. In another aspect, the polypeptide comprises or consists of the mature polypeptide of SEQ ID NO: 12.

In another embodiment, the present invention relates to an isolated polypeptide having pectin lyase activity encoded by a polynucleotide having a sequence identity to the mature polypeptide coding sequence of SEQ ID NO: 9 or SEQ ID NO: 11, or the cDNA sequence thereof of at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 10 or SEQ ID NO: 12 comprising a substitution, deletion, and/or insertion at one or more (e.g., several) positions. In an embodiment, the number of amino acid substitutions, deletions and/or insertions introduced into the mature polypeptide of SEQ ID NO: 10 or SEQ ID NO: 12 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for pectin lyase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

Sources of Polypeptides Having Xylanase Activity

A polypeptide having xylanase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a Gram-positive bacterial polypeptide such as a *Bacillus*, *Clostridium*, *Enterococcus*, *Geobacillus*, *Lactobacillus*, *Lactococcus*, *Oceanobacillus*, *Staphylococcus*, *Streptococcus*, or *Streptomyces* polypeptide having pectin lyase activity, or a Gram-negative bacterial polypeptide such as a *Campylobacter*, *E. coli*, *Flavobacterium*, *Fusobacterium*, *Helicobacter*, *Ilyobacter*, *Neisseria*, *Pseudomonas*, *Salmonella*, or *Ureaplasma* polypeptide.

In one aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polypeptide.

In another aspect, the polypeptide is a *Streptococcus equisimilis*, *Streptococcus pyogenes*, *Streptococcus uberis*, or *Streptococcus equi* subsp. *Zooepidemicus* polypeptide.

In another aspect, the polypeptide is a *Streptomyces achromogenes*, *Streptomyces avermitilis*, *Streptomyces coelicolor*, *Streptomyces griseus*, or *Streptomyces lividans* polypeptide.

The polypeptide may be a fungal polypeptide. For example, the polypeptide may be a yeast polypeptide such as a *Candida*, *Kluyveromyces*, *Pichia*, *Saccharomyces*, *Schizosaccharomyces*, or *Yarrowia* polypeptide; or a filamentous fungal polypeptide such as an *Acremonium*, *Agaricus*, *Alternaria*, *Aspergillus*, *Aureobasidium*, *Botryosphaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, Irpex, *Lentinula*, Leptospaeria, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide.

In another aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide.

In another aspect, the polypeptide is an *Acremonium cellulolyticus*, *Aspergillus aculeatus*, *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thiela-* via australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei, or Trichoderma viride polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and *Agricultural Research* Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application, Academic Press*, New York. Other nucleic acid amplification procedures such as ligase chain reaction (LCR), ligation activated transcription (LAT) and polynucleotide-based amplification (NASBA) may be used.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 9 or SEQ ID NO: 11 or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, Aspergillus oryzae TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

The control sequence may also be an mRNA stabilizer region downstream of a promoter and upstream of the coding sequence of a gene which increases expression of the gene.

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide.

The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus* eryngii, *Thielavia*

*terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787.

Methods of Production

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Enzyme Compositions

The present invention also relates to compositions comprising a polypeptide of the present invention.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

Preferred Embodiments

The invention is further described by following numbered embodiments:

1. A method to improve the total starch yield and/or gluten yield from corn kernels in a wet milling process, the method comprising admixing corn kernels or a fraction of the corn kernels with an enzyme composition comprising an effective amount of one or more hydrolytic enzymes, wherein at least one of said hydrolytic enzymes is selected from the group consisting of a GH30 polypeptide, a GH5 polypeptide or a combination thereof.

2. The method according to embodiment 1, wherein the amount of starch and/or gluten released from fiber during the wet milling process is increased.

3. The method according to any of the preceding embodiments, comprising the steps of:
   a) soaking the corn kernels in water to produce soaked kernels;
   b) grinding the soaked kernels to produce soaked and ground kernels;
   c) separating germs from the soaked and ground kernels to produce a corn kernel mass comprising fiber, starch and gluten; and
   d) subjecting the resultant corn kernel mass to a fiber washing procedure.

4. The method according to any of the preceding embodiments, wherein said corn kernels or a fraction of said corn kernels is admixed with said one or more hydrolytic enzymes, before, during or after step d) according to embodiment 3.

5. The method according to any of the preceding embodiments, wherein said corn kernels or a fraction of said corn kernels is admixed with said one or more hydrolytic enzymes during step d) according to embodiment 3.

6. The method according to any of the preceding embodiments, wherein said corn kernels or a fraction of said corn kernels is allowed to react with said one or more hydrolytic enzymes for at least 15 minutes.

7. The method according to any of embodiment 3-6, wherein said fiber washing procedure comprises the use of a fiber washing system optimized for introduction of one or more hydrolytic enzymes and wherein the fiber washing system comprise a space configured to provide a total retention time in the fiber washing system of at least 35 minutes and less than 48 hours.

8. The method according to any of the preceding embodiments, wherein the incubation time in said space configured into the fiber washing system is at least 5 minutes and less than 48 hours.

9. The method according to any of the preceding embodiments, wherein the incubation temperature is between 25° C. and 95° C.

10. The method according to any of the preceding embodiments, wherein said GH5 polypeptide has xylanase activity.

11. The method according to any of the preceding embodiments, wherein said GH30 polypeptide has xylanase activity.

12. The method according to any of the preceding embodiments, wherein said GH5 polypeptide further comprise one or more of the following activities: endo-β-1,4-glucanase/cellulase (EC 3.2.1.4) activity and/or endo-β-1,4-xylanase (EC 3.2.1.8) activity and/or β-glucosidase (EC 3.2.1.21) activity and/or β-mannosidase (EC 3.2.1.25) activity and/or β-glucosylceramidase (EC 3.2.1.45) activity and/or glucan β-1,3-glucosidase (EC 3.2.1.58) activity and/or licheninase (EC 3.2.1.73) activity and/or exo-β-1,4-glucanase/cellodextrinase (EC 3.2.1.74) activity and/or glucan endo-1,6-β-glucosidase (EC 3.2.1.75) activity and/or mannan endo-β-1,4-mannosidase (EC 3.2.1.78) activity and/or cellulose β-1,4-cellobiosidase (EC 3.2.1.91) activity and/or steryl β-glucosidase (EC 3.2.1.104) activity or endoglycoceramidase (EC 3.2.1.123) activity and/or chitosanase (EC 3.2.1.132) activity and/or β-primeverosidase (EC 3.2.1.149) activity and/or xyloglucan-specific endo-β-1,4-glucanase (EC 3.2.1.151) activity and/or endo-β-1,6-galactanase (EC 3.2.1.164) activity and/or hesperidin 6-O-α-L-rhamnosyl-βglucosidase (EC 3.2.1.168) activity and/or β-1,3-mannanase (EC 3.2.1.-) activity and/or arabinoxylan-specific endo-β-1,4-xylanase (EC 3.2.1.-) activity and/or mannan transglycosylase (EC 2.4.1.-) activity.

13. The method according to any of the preceding embodiments, wherein said GH30 polypeptide further comprise one or more of the following activities: endo-β-1,4-xylanase (EC 3.2.1.8) activity and/or β-glucosidase (EC 3.2.1.21) activity and/or β-glucuronidase (EC 3.2.1.31) activity and/or β-xylosidase (EC 3.2.1.37) activity and/or β-fucosidase (EC 3.2.1.38) activity and/or glucosylceramidase (EC 3.2.1.45) activity and/or β-1,6-glucanase (EC 3.2.1.75) activity and/or glucuronoarabinoxylan endo-β-1,4-xylanase (EC 3.2.1.136) activity and/or endo-β-1,6-galactanase (EC:3.2.1.164) activity and/or [reducing end] β-xylosidase (EC 3.2.1.-) activity.

14. The method according to any of the preceding embodiments, wherein the GH5 polypeptide is selected from a group consisting of:
i) A mature polypeptide of the amino acid sequence set forth in SEQ ID NO: 1-3, SEQ ID NO: 8, SEQ ID NO: 10 or SEQ ID NO: 12;
ii) A mature polypeptide, which has at least 60% identity to the mature polypeptide in i)
iii) A subsequence of any one of the mature polypeptides in i) and ii).

15. The method according to any of the preceding embodiments, wherein the GH30 polypeptide is selected from a group consisting of:
i) A mature polypeptide of the amino acid sequence set forth in SEQ ID NO: 4; SEQ ID NO:5; SEQ ID NO:6, or SEQ ID NO:7;
ii) A mature polypeptide, which has at least 60% identity to the mature polypeptide in i)
iii) A subsequence of any one of the mature polypeptides in i) and ii).

16. The method according to any of the preceding embodiments, wherein said enzyme composition comprising one or more hydrolytic enzymes further comprise one or more enzymes selected form the group consisting of: cellulases (EC 3.2.1.4), xylanases (EC 3.2.1.8) arabinofuranosidases (EC 3.2.1.55 (Non-reducing end alpha-L-arabinofuranosidases); EC 3.2.1.185 (Non-reducing end beta-L-arabinofuranosidases) cellobiohydrolase I (EC 3.2.1.150), cellobiohydrolase II (E.C. 3.2.1.91), cellobiosidase (E.C. 3.2.1.176), beta-glucosidase (E.C. 3.2.1.21), beta-xylosidases (EC 3.2.1.37) or proteases (E.C XXXX).

17. The method according to any of the preceding embodiments, wherein the one or more hydrolytic enzymes is expressed in an organism with a cellulase background, such as *Trichoderma reesei*.

18. The method according to any of the preceding embodiments, wherein the one or more hydrolytic enzymes are purified.

19. The method according to any of the preceding embodiments, wherein the one or more hydrolytic enzymes is/are in a liquid composition.

20. The method according to any of the preceding embodiments, wherein the one or more hydrolytic enzymes is/are in a solid composition.

21. The method according to any of the preceding embodiments, wherein the effective amount of one or more hydrolytic enzymes admixed with one or more fractions of said corn kernel mass, is between 0.005-0.5 kg enzyme protein/metric tonne corn kernels entering the wet milling process.

22. A composition comprising corn fiber, said composition being obtainable by the method described in any of embodiments 1-21.

23. Use of a GH30 polypeptide and/or a GH5 polypeptide in a method to improve the total starch yield and/or gluten yield from corn kernels in a wet milling process as defined in any of embodiments 1-21.

24. An isolated polypeptide having xylanase activity, selected from the group consisting of:
(a) a polypeptide having at least 80% sequence identity to the mature polypeptide of SEQ ID NO: 10 or SEQ ID NO: 12;
(b) a polypeptide encoded by a polynucleotide having least 80% sequence identity to the mature polypeptide coding sequence of SEQ ID NO: 9 or SEQ ID NO: 11 or the cDNA sequence thereof;
(c) a variant of the mature polypeptide of SEQ ID NO: 10 or SEQ ID NO: 12 comprising a substitution, deletion, and/or insertion at one or more positions; and
(d) a fragment of the polypeptide of (a), (b), or (c) that has pectin lyase activity.

25. The polypeptide of embodiment 24, having at least 88%, at least 89%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 10 or SEQ ID NO: 12.

26. The polypeptide of embodiment 24 or 25, which is encoded by a polynucleotide that hybridizes under medium-high stringency conditions to very high stringency conditions with (i) the mature polypeptide coding sequence of SEQ ID NO: 9 or SEQ ID NO: 11, (ii) the cDNA sequence thereof, or (iii) the full-length complement of (i) or (ii).

27. The polypeptide of any of embodiments 24-26, which is encoded by a polynucleotide having at least 88%, at least 89%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 10 or SEQ ID NO: 12 or the cDNA sequence thereof.

28. The polypeptide of any of embodiments 24-27, comprising or consisting of SEQ ID NO: 10 or SEQ ID NO; 12; or the mature polypeptide of SEQ ID NO: 0 or SEQ ID NO: 1.

29. A composition comprising the polypeptide of any of embodiments 24-28.

30. An isolated polynucleotide encoding the polypeptide of any of embodiments 24-28.

31. A nucleic acid construct or expression vector comprising the polynucleotide of embodiment 30 operably linked to one or more control sequences that direct the production of the polypeptide in an expression host.

32. A recombinant host cell comprising the polynucleotide of embodiment 30 operably linked to one or more control sequences that direct the production of the polypeptide.

33. A method of producing a polypeptide having xylanase activity, comprising the steps of:
a) cultivating the host cell of embodiment 32 under conditions conducive for production of the polypeptide; and, optionally,
b) recovering the polypeptide.

EXAMPLES

Example 1

In this example, the amount of starch and gluten separated from fiber, after incubation with and without enzyme, was measured.

The fiber sample was obtained from a wet-mill plant after fiber pressing with a total dry matter content of 20%. The sample was re-suspended in buffer (pH 4, 0.02M Na Acetate) to 100-g slurry containing 5% dry solids. To this slurry enzyme was added at a final ratio of 350 µg per g dry-solids substrate (DS). See sample details in table 1.

TABLE 1

Table 1: Temperature and enzyme composition in each sample tested.

| Sample ID | Temperature (° C.) | Cellulolytic enzymes* (µg EP/g DS) | GH5^ (µg EP/g DS) | GH30" (µg EP/g DS) |
|---|---|---|---|---|
| 1 | 40 | 280 | 70 | 0 |
| 2 | 40 | 280 | 0 | 70 |
| 3 | 40 | 0 | 0 | 0 |
| 4 | 52 | 280 | 70 | 0 |
| 5 | 52 | 280 | 0 | 70 |
| 6 | 40 | 280 | 35 | 35 |
| 7 | 52 | 350 | 0 | 0 |
| 8 | 40 | 350 | 0 | 0 |

*The cellulolytic enzymes composition used is Celluclast ® from Novozymes.
^The GH5 polypeptide used is the mature polypeptide of SEQ ID NO: 3.
"The GH30 polypeptide used is the mature polypeptide of SEQ ID NO: 4.

The samples were incubated at a temperature of 52° and 40° C. (See table 1) in an air-heated incubator with constant shaking for 120 minutes. After incubation, the samples were cooled quickly in ice-water (5° C.) before processing. The slurry was transferred on to a 150-micron sieve, while collecting the filtrate passing through.

The fiber that retained over the sieve was pressed using a spatula to recover as much filtrate as possible. The pressed fiber was then transferred to a beaker containing 200-ml of water and stirred. The slurry was passed through the 150-micron sieve and the collected filtrate was combined with the first. The pressing, washing and filtering steps above was repeated once more, so that a final filtrate is recovered and combined with the first two. The combined filtrate was then vacuum filtered, this time through a glass micro filter paper (WHATMAN) which retains the insoluble solids that were released from the fiber and passed through the 150-micron screen. After passing 200 ml water over the filter paper to remove any trace of solubles, the total insoluble solids retained on the filter paper is dried and weighed. The dry weight is reported as Starch+Gluten released as percentage (w/w) of fiber dry matter of starting substrate. The results are shown in table 2.

TABLE 2

| Sample ID | Temperature | Enzymes | Starch + Gluten Released (% (w/w) of fiber dry matter) |
|---|---|---|---|
| 1 | 40° C. | GH5 + Cellulolytic enzymes | 22% |
| 2 | 40° C. | GH30 + Cellulolytic enzymes | 19% |
| 3 | 40° C. | No Enzymes | 11% |
| 4 | 52° C. | GH5 + Cellulolytic enzymes | 23% |
| 5 | 52° C. | GH30 + Cellulolytic enzymes | 19% |
| 6 | 40° C. | GH5 and GH30 + Cellulolytic enzymes | 21% |
| 7 | 52° C. | Cellulolytic enzymes | 12% |
| 8 | 40° C. | Cellulolytic enzymes | 12% |

The effect of GH5 and/or GH30 enzyme addition is apparent from the increase in starch and gluten yields at 40° C. and 52° C.

Example 2

Enzymes:

GH30 Xylanase A: GH30 xylanase derived from *Bacillus subtilis* (SEQ ID NO:5)

GH30 Xylanase B: GH30 xylanase derived from *Bacillus subtilis* (SEQ ID NO:6)

GH30 Xylanase C: GH30 xylanase derived from *Bacillus subtilis* (SEQ ID NO:7)

CELLUCLAST/CELLUCLAST 1.5 L: A commercially available cellulase composition (NOVOZYMES A/S, Denmark).

A 10-g fiber assay was performed at pH 3.8, with incubation at 52° C. for 1 hour and a dosage of 35 ug enzyme protein per gram corn; using enzyme blends containing GH30 Xylanase A, GH30 Xylanase B or GH30 Xylanase C, in combination with CELLUCLAST. The Blends consisted of 20% (w/w) GH30 Xylanase A, GH30 Xylanase B or GH30 Xylanase C, and the remaining 80% (w/w) from CELLUCLAST. For comparison, an enzyme composition containing only CELLUCLAST was included. A corn fiber with 15.52% residual starch and 12.00% residual protein in fiber was used as substrate in the fiber assay. Release of starch+gluten (dry substance) from the corn fiber at the specified dosage was measured; the results are provided in the table below.

TABLE 3

| Treatments | Dose (ug enzyme protein/g corn) | Starch + Gluten Recovered |
|---|---|---|
| No Enzyme | 0 | 4.39% |
| Celluclast only | 35 | 6.68% |
| Celluclast + GH30 Xylanase A | 35 | 8.66% |
| Celluclast + GH30 Xylanase B | 35 | 8.23% |
| Celluclast + GH30 Xylanase C | 35 | 7.83% |

The addition of GH30 Xylanase A, GH30 Xylanase B and GH30 Xylanase C in combination with a cellulase enzyme, such as, CELLUCLAST, can significantly increase the yield of starch +gluten in a corn wet-milling process.

Example 3: Laboratory Corn Wet-Mill Fiber Treatment with GH5 Xylanase

Enzymes:
GH5 Xylanase: GH5_21 xylanase derived Cryseobacterium sp., having the amino acid sequence of the mature protein of SEQ ID NO: 8 (SEQ ID NO: 26 of WO 2016/005522).
Enzyme cocktail D: consists mainly of cellobiohydrolases (CBH I and II), from an exogenous donor, and endoglucanases (EG1 and 2) from the native Trichoderma host.
Enzyme cocktail T: consists mainly (~80%) of cellobiohydrolases and endoglucanases from the native Trichoderma host, and remaining ~20% of total protein consisting of xylanase GH10 from an exogenous donor.
FRONTIA FIBERWASH® is a commercial product, consisting of a cocktail of xylanases and cellulases. (NOVOZYMES A/S, Denmark).
The 10-g fiber assay generally includes incubating wet fiber samples obtained from wet-milling plant, in the presence of enzymes, at conditions relevant to the process (pH 3.5 to 4, Temp around 52° C.) and over a time period of between 1 to 4 hr. After incubation, the fiber is transferred and pressed over a screen (typically 75 micron or smaller), where the filtrates consisting mainly of the separated starch and gluten are then collected. A number of washes are done over the screen, and the washings are collected together with the initial filtrate. The collected filtrate are then passed over a funnel filter (glass filter with 0.45 micron opening) to further separate the insoluble solids (mostly starch and gluten) from the rest of the filtrates (mostly dissolved solids). These recovered insoluble solids are washed and then oven dried to dryness. The insoluble dry mass is weighed and then analyzed for starch content, using a modification of Ewers method (acid hydrolysis and measurement of glucose by liquid chromatography).
10-g fiber assay is performed at pH 4, incubating fiber at 50° C. for 2 hour with different enzyme treatments as described in the following. Control is fiber incubation without any enzyme added. FRONTIA FIBERWASH® is a commercial product used for this industrial application, consisting of a cocktail of xylanases and cellulases. GH5 is dosed in combination with two different enzyme cocktails, both of which are derived from Trichoderma reesei fermentations. GH5 was dosed at 20% of the total enzyme protein added, with the remaining 80% consisting of the enzyme cocktail background. The total amount of enzyme proteins added in all treatments was 500 micrograms per gram dry fiber. Enzyme cocktail D consists mainly of cellobiohydrolases (CBH I and II), from an exogenous donor, and endoglucanases (EG1 and 2) from the native Trichoderma host. Enzyme cocktail T consists mainly (~80%) of cellobiohydrolases and endoglucanases from the native Trichoderma host, and remaining ~20% of total protein consisting of xylanase GH10 from an exogenous donor. Results are reported in Table below:

TABLE 4

| Enzyme Blend Treatment | Insoluble solids recovered (% wt of starting dry fiber) | Starch recovered (% wt of starting dry fiber) |
|---|---|---|
| Control (no enzyme added) | 3.60% (±0.01) | 2.48% (±0.05) |
| Frontia Fiberwash ® | 10.61% (±0.51%) | 7.81% (±0.22%) |
| GH5 + cocktail D | 13.16% (±0.38%) | 9.25% (±0.51%) |
| GH5 + cocktail T | 12.72% (±0.53%) | 8.77% (±0.26%) |

(±one standard deviation, n = 3)

Example 4

Method Description 15 mL Fiber Washing Assay
The 15 mL fine fiber assay generally includes incubating wet fine fiber samples obtained from a corn wet-milling plant in the presence of enzymes, at conditions relevant to the process (pH 4.0, temp approximately 40° C.) with thorough mixing in a hybridization incubator for one hour. After incubation, the fiber is vacuum filtered through a MILLIPORE steriflip tube top filter unit. The fiber is resuspended to a volume of 30 mL with distilled water, thoroughly vortexed and vacuumed filtered a second time. The collected filtrate consists of the extracted starch and gluten. The filtrate is centrifuged in an AVANTI J-E at 5,000 rpm for 7 minutes to pellet the starch. The supernatant is slowly removed using a 50 mL serological pipette as to not disturb the starch and gluten pellet. This washing and centrifugation procedure is repeated twice more to remove solubilized oligomers.
After washing, a total volume of 5 mL remains, including starch pellet. The excess water is removed using a EZ-2 ELITE Solvent Evaporator (method: aqueous, maximum 65° C., 3 hours, 3,000 rpm, 120 mbar). After this, the pellet (containing starch and gluten) is resuspended in 500 uL of 1.6M hydrochloric acid and heated at 90° C. for 45 minutes, 1,000 rpm. This incubation breaks down the starch granule into sugar monomers. After acid hydrolysis, the reaction is quenched using 625 uL of 1.4M sodium hydroxide and cooled to room temperature. The amount of reducing sugars is then determined via the addition of 345 uL of dinitrosalicyclic acid reagent (DNS). Samples are incubated for 10 minutes at 95° C., 300 rpm. The available reducing sugars react with the DNS causing an increase in the red-orange spectra (Miller, Analytical Chemistry 1959). The samples are then centrifuged at 5,000 rpm, 30 seconds to collect condensate and cooled to ambient temperature. 800 uL of each sample is transferred to a 96 deep well plate, and diluted in distilled water using a multichannel pipette. 200 uL is then transferred using a multichannel pipette to a NUNC F 96 well plate. Absorbance at 560 nanometers (nm) is read using a TECAN Infinite M1000.
GH5 Improvement Over FRONTIA FIBERWASH®
The 15 mL fine fiber assay is performed at pH 4, incubating fiber for one hour at 40° C. with different enzyme treatments. Control is fiber incubation with no enzyme. FRONTIA FIBERWASH® is a commercial enzyme used for releasing starch from fibres in a wet milling process. GH5 Blend consist of a complete Trichoderma reesei cellulose complex (80%) and the GH5 xylanase having the amino acid sequence of the mature protein of SEQ ID NO:8 (20%). All enzyme blends were added with a total of 500 micrograms of enzyme protein per gram dried fiber solids (ug/gDS). All treatments were run in triplicate. Absorbance was read at 560 nm, and converted to glucose (g/L) using a glucose standard. The calculated glucose was then normalized using fiber dry solids and reported as starch released from fiber. Absorbance values and starch release from fiber are reported in Table 5.

TABLE 5

Results from 15 mL fiber assay

| Treatment Blend | Average Absorption (560 nm) | Starch Release from Fiber (%) |
|---|---|---|
| Control Frontia | 0.171 (0.047) | 1.82 (0.009) |
| Fiberwash ® | 0.379 (0.117) | 5.83 (0.022) |
| GH5 Blend | 0.576 (0.200) | 9.69 (0.40) |

(±standard deviation, n = 3)

Example 5—GH5 Diversity

The 15 mL fine fiber assay is performed at pH 4, incubating fiber for one hour at 40° C. with different enzyme treatments in Table 6. Control is fiber incubation with no enzyme. All enzyme blends contained the 400 ug/gDS of *T. reesei* (Control). Auxiliary GH5's were added to the appropriate treatments at 25 ug/gDS as indicated in Table 6.

Absorbance was read at 560 nm, and converted to glucose (g/L) using a glucose standard. The calculated glucose was then normalized using fiber dry solids and reported as starch released from fiber. Absorbance values and starch release from fiber are reported in Table 7.

TABLE 7

GH5 diversity tested

| Treatment Blend | GH5 subfamily | Sequence |
|---|---|---|
| *Chrysobacterium* sp - 10696* | GH5_21 | SEQ ID NO: 8 |
| *Sphingobacterium* sp-64162i | GH5_21 | SEQ ID NO: 9 |
| *Bacillus hemicellulosilyticus* JCM 9152 | GH5_35 | SEQ ID NO: 10 |

*Includes n-his tag. All wild type enzymes have n-his tag, which has been shown to lower enzyme activity.

TABLE 8

GH5 diversity results

| Treatment Blend | Average Absorption (560 nm) | Starch Release from Fiber (%) |
|---|---|---|
| Control | 0.331 (0.097) | 5.99 (0.023) |
| *Chrysobacterium* sp - 10696* | 0.368 (0.022) | 6.90 (0.025) |
| *Sphingobacterium* sp-64162i | 0.408 (0.024) | 7.70 (0.006) |
| *Bacillus hemicellulosilyticus* JCM 9152 | 0.365 (0.013) | 6.82 (0.007) |

(±standard deviation, n = 3)

The invention claimed is:

1. A method of treating corn kernels, comprising a wet milling process which comprises:
(a) soaking the corn kernels in water to produce soaked corn kernels;
(b) grinding the soaked corn kernels to produce soaked and ground corn kernels;
(c) separating germs from the soaked and ground corn kernels to produce a corn kernel mass comprising fiber, starch and gluten; and
(d) subjecting the corn kernel mass to a fiber washing procedure to separate the fiber from the starch and gluten, wherein the fiber washing procedure comprises a fiber washing system comprising:
(i) 2-8 screen units which are fluidly connected in a counter current washing configuration including a first screen unit (S1) and a last screen unit, wherein each screen unit is configured for separating a stream of corn kernel mass and liquid into a first fraction (s) and a second fraction (f), wherein the second fraction (f) contains a higher amount of fiber than the first fraction (s);
(ii) a space (V) which is located between the first (S1) and the last screen units and is fluidly connected to receive one of the first fractions (s), one of the second fractions (f), or a mixed first and second fraction (s,f); and
wherein subjecting the corn kernel mass to the fiber washing procedure comprises:
(i) introducing the corn kernel mass to the first screen unit (S1);
(ii) introducing process water to the last screen unit;
(iii) introducing an enzyme composition comprising a GH5 xylanase downstream of the first screen unit (S1) and upstream of the last screen unit and upstream of or in the space (V);
(iv) contacting at least one of the first fraction (s), at least one of the second fraction (f), or at least one mixed first and second fraction (s,f) of the corn kernel mass with the enzyme composition comprising the GH5 xylanase for a total retention time of from 90 minutes to 5 hours in the fiber washing system, and incubating the at least one of the first fraction (s), the at least one of the second fraction (s,f), or the at least one mixed first and second fraction (s,f) in the space (V) for an incubation time of from 0.5 to 3 hours to produce an incubated fraction; and
(v) outletting the incubated fraction to a downstream screen unit; and
wherein the first fraction (s) outlet from each screen unit is a product stream containing starch and gluten and the second fraction (f) outlet from each screen unit is a washed corn kernel mass containing fiber and a lower amount of starch and gluten than the corn kernel mass entering the screen unit.

2. The method of claim 1, wherein the fiber washing system has 4 screen units including a second screen unit, a third screen unit and a fourth screen unit being the last screen unit and the enzyme composition is introduced in the second or third screen unit or in the space (V).

3. The method of claim 2, wherein the enzyme composition is introduced in the second screen unit or the space (V) wherein the space (V) is located between the second and third screen units.

4. The method of claim 1, wherein the fiber washing system has 5 screen units including a second screen unit, a third screen unit, a fourth screen unit and a fifth screen unit being the last screen unit and the enzyme composition is introduced in the second, third or fourth screen unit, or in the space (V).

5. The method of claim 4, wherein the enzyme composition is introduced in the third screen unit or the space (V) wherein the space (V) is located between the third and fourth screen units.

6. The method of claim 1, wherein the fiber washing system has 6 screen units including a second screen unit, a third screen unit, a fourth screen unit, a fifth screen unit and a sixth screen unit being the last screen unit and the enzyme composition is introduced in the second, third, fourth or fifth screen unit, or in the space (V).

7. The method of claim 6, wherein the enzyme composition is introduced in the fourth screen unit or the space (V) wherein the space (V) is located between the fourth and fifth screen units.

8. The method of claim 1, wherein the fiber washing system has 7 screen units including a second screen unit, a third screen unit, a fourth screen unit, a fifth screen unit, a sixth screen unit and a seventh screen unit being the last screen unit and the enzyme composition is introduced in the second, third, fourth, fifth or sixth screen unit, or in the space (V).

9. The method of claim 8, wherein the enzyme composition is introduced in the fourth screen unit or the space (V) wherein the space (V) is located between the fourth and fifth screen units.

10. The method of claim 1, wherein the fiber washing system has 8 screen units including a second screen unit, a third screen unit, a fourth screen unit, a fifth screen unit, a sixth screen unit, a seventh screen unit and an eighth screen unit being the last screen unit and the enzyme composition is introduced in the second, third, fourth, fifth, sixth or seventh screen unit, or in the space (V).

11. The method of claim 10, wherein the enzyme composition is introduced in the fifth screen unit or the space (V) wherein the space (V) is located between the fifth and sixth screen units.

12. The method of claim 1, wherein the space (V) has an incubation temperature between 25° C. and 95° C.

13. The method of claim 1, wherein the GH5 xylanase has at least 90% sequence identity to any mature polypeptide of SEQ ID NO: 1-3, SEQ ID NO: 8, SEQ ID NO: 10 or SEQ ID NO: 12.

14. The method of claim 1, wherein the enzyme composition further comprises one or more hydrolytic enzymes selected form the group consisting of cellulases (EC 3.2.1.4), xylanases (EC 3.2.1.8), arabinofuranosidases (EC 3.2.1.55), non-reducing end beta-L-arabinofuranosidases (EC 3.2.1.185), cellobiohydrolase I (EC 3.2.1.150), cellobiohydrolase II (E.C. 3.2.1.91), cellobiosidase (E.C. 3.2.1.176), beta-glucosidase (E.C. 3.2.1.21), beta-xylosidases (EC 3.2.1.37) or proteases.

15. The method of claim 14, wherein the one or more hydrolytic enzymes are expressed in *Trichoderma reesei*.

16. The method of claim 1, wherein the enzyme composition is a liquid composition.

17. The method of claim 1, wherein the enzyme composition is a solid composition.

18. The method of claim 1, wherein the enzyme composition is added in an amount between 0.005-0.5 kg enzyme protein/metric tonne corn kernels entering the wet milling process.

19. The method of claim 1, further comprising separating the starch from the gluten contained in in the first fraction (s) from the last screen unit of the fiber washing system.

20. The method of claim 19, further comprising washing the starch.

* * * * *

SEQUENCE LISTING

```
<160> NUMBER OF SEQ ID NOS: 12

<210> SEQ ID NO 1
<211> LENGTH: 655
<212> TYPE: PRT
<213> ORGANISM: Ruminiclostridium thermocellum

<400> SEQUENCE: 1

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala His His His His
            20                  25                  30

His Pro Arg Ala Asp Pro Gln Arg Gly Arg Pro Tyr Leu Asn Ser Ala
        35                  40                  45

Arg Thr Thr Phe Val Gly Asp Asn Gly Gln Pro Leu Arg Gly Pro Tyr
    50                  55                  60

Ile Ser Thr Glu Trp Thr Ser Ala Ala Pro Tyr Asp Gln Ile Ala Arg
65                  70                  75                  80

Ile Lys Asn Leu Gly Phe Asn Ala Val His His Tyr Ala Glu Cys Phe
                85                  90                  95

Asp Ile Asn Tyr Pro Asn Ala Gly Ser Lys Ser Pro Gly Tyr Ala Ala
            100                 105                 110

Thr Glu Ile Asp Lys Val Val Glu Arg Thr Arg Glu Leu Gly Leu Tyr
        115                 120                 125

Leu Val Met Thr Ile Gly Asn Gly Ala Asn Asn Gly Asn His Asn Thr
    130                 135                 140

Arg Tyr Ala Lys Asp Phe Trp Ser Phe Tyr Ser Ser Arg Tyr Ala Asn
145                 150                 155                 160
```

-continued

```
Glu Thr His Val Leu Tyr Glu Ile His Asn Glu Pro Val Ala Trp Gly
            165                 170                 175

Pro Pro Tyr Ser Ser Thr Thr Ala Thr Pro Thr Gly Ala Val Glu Met
            180                 185                 190

Asn Val Asp Val Tyr Lys Thr Ile Arg Ala Asn Ala Pro Lys Thr Pro
            195                 200                 205

Val Leu Ile Phe Ser Tyr Ser Val Phe Gly Thr Gly Gly Thr Thr
        210                 215                 220

Glu Ala Leu Lys Asp Ile Gln Ala Phe Asn Ser Ala Val Phe Gly Lys
225                 230                 235                 240

Gln Asp Ala Val Trp Thr Asn Glu Ala Val Ala Phe His Gly Tyr Ala
                245                 250                 255

Gly Trp Glu Ala Thr Ser Thr Ala Val Asp Gly Leu Leu Lys Ala Gly
            260                 265                 270

Tyr Pro Cys Phe Met Thr Glu Tyr Ala Gly Gly Ala Trp Gly Ser Gly
        275                 280                 285

Thr Gly Gly Phe Asp Ile Gln Leu Thr Ser Glu Leu Glu Arg Met Gly
    290                 295                 300

Val Ser Trp Leu Thr Phe Gln Tyr Ile Pro Pro Ser Gly Val Ser Asp
305                 310                 315                 320

Asp Val Thr Lys Pro Glu Tyr Phe Ser Ala Leu Val Glu Asn Ala Gly
                325                 330                 335

Leu Ser Trp Lys Pro Asp Tyr Gly Asn Trp Pro Ala Ala Arg Gly Val
            340                 345                 350

His Gly Asn Gly Gly Leu Pro Arg Lys Thr Ser Thr Trp Val Asn Asn
        355                 360                 365

Phe Leu Thr Gly Thr Thr Arg Ile Glu Ala Glu Asp Phe Asp Trp Gly
    370                 375                 380

Gly Asn Asp Val Ser Phe Tyr Asp Lys Asp Ser Glu Asn Lys Gly Ala
385                 390                 395                 400

Gln Tyr Arg Leu Asp Glu Ala Val Asp Ile Glu Thr Thr Lys Asp Ala
                405                 410                 415

Asp Gly Gly Tyr Asn Val Gly Trp Ile Glu Asp Gly Glu Trp Leu Glu
            420                 425                 430

Tyr Thr Ile Trp Val Gln His Pro Gly Tyr Tyr Asn Leu Ala Leu Arg
        435                 440                 445

Val Ala Asn Asn Ser Gly Gly Ser Val Gln Val Asn Phe Gly Asn Gln
    450                 455                 460

Asp Lys Thr Gly Thr Trp Val Leu Pro Val Thr Gly Gly Val Gln Thr
465                 470                 475                 480

Trp Lys Thr Asp Thr Arg Gln Val Phe Leu Gly Ser Gly Arg Gln Lys
                485                 490                 495

Leu Arg Ile Asn Ala Leu Ser Gly Gly Phe Asn Leu Asn Trp Ile Glu
            500                 505                 510

Leu Ser Pro Val Ser Thr Gly Pro Ile Ala Asp Gly Thr Tyr Lys Phe
        515                 520                 525

Leu Asn Arg Ala Asn Thr Met Thr Leu Gln Glu Val Thr Ser Asn Asn
    530                 535                 540

Ser Ile Val Thr Ser Tyr Lys Gly Thr Ala Asp Gln His Trp Lys
545                 550                 555                 560

Ile Gln His Ile Gly Gly Gln Tyr Arg Ile Ser Ser Ala Gly Arg
                565                 570                 575

Gly Trp Asn Trp Asn Trp Trp Met Gly Phe Gly Thr Val Gly Trp Trp
```

```
            580             585              590
Gly Thr Gly Ser Gly Thr Cys Phe Ile Ile Arg Pro Thr Gly Asp Gly
            595              600              605

Tyr Tyr Arg Phe Val Leu Val Asn Asp Gly Thr Asn Leu Glu Ile Ser
            610              615              620

Asn Asn Asp Ser Ser Lys Ile Glu Gly Lys Ala Tyr His Glu Gly Ala
625              630              635              640

Asn Gln Gln Trp Ala Ile Gln Leu Pro Ser Ala Val Phe Pro
            645              650              655

<210> SEQ ID NO 2
<211> LENGTH: 555
<212> TYPE: PRT
<213> ORGANISM: Paenibacillus sp-18054

<400> SEQUENCE: 2

His His His His His His Pro Arg Leu Thr Val Pro Pro Gly Ala Pro
1               5                   10                  15

Ala Glu Ala Trp Ser Gly Met Pro Thr Pro Lys Leu His Val Ser Gly
            20                  25                  30

Asn Gln Leu Val Asn Ala Asn Gly Gln Pro Val Leu Leu Ser Gly Trp
        35                  40                  45

His Gln Pro Ser Gly Ser Tyr Trp Thr Tyr Gln Ser Ser Ser Tyr Tyr
    50                  55                  60

Leu Asp Arg Asn Gly Gly Asn Arg His Ala Ala Asn Leu Ala Tyr Leu
65                  70                  75                  80

Lys Asp Ile Thr Asp Thr Phe Thr Asp Thr Ser Pro Lys Tyr Gly Asn
                85                  90                  95

Asn His Gly Trp Tyr Met Asn Gln Val Arg Leu Phe Ile Asp Arg Glu
            100                 105                 110

Asp Met Gly Asp Val Ala Glu Gly Thr Tyr Asn Phe Ala Gly Leu Gln
        115                 120                 125

Ala Val Thr Gln Asn Val Ile Ile Pro Tyr Ile Asn Tyr Ala Arg Thr
    130                 135                 140

Lys Gly Leu Tyr Val Thr Leu Gly Leu Asp Phe Thr Leu Lys Asp Asn
145                 150                 155                 160

Gln Ala Thr Thr Gln Ala Asn Leu Asp Lys Phe Asn Gln Ile Trp Ser
                165                 170                 175

Tyr Leu Ala Ser Arg Pro Glu Ile Arg Ser Ala Asp Asn Val Met Phe
            180                 185                 190

Glu Ile Ile Asn Glu Pro Val Leu Ser Tyr Ala Asp Gly Arg Trp Gly
        195                 200                 205

Gly His Pro Ser Asp Pro His Phe Ile Ala Phe Trp Asn Asp Leu Arg
    210                 215                 220

Ser Phe Gln Asn Ser Ile Ile Ser Ser Ile Arg Ala Gln Gly Ala Asp
225                 230                 235                 240

Asn Val Ile Trp Ala Ala Gly Leu Gly Trp Asp Gln Tyr Tyr Gln Leu
                245                 250                 255

Cys Ala Ser His Pro Leu Thr Asp Pro Leu Asn Asn Val Gly Tyr Ala
            260                 265                 270

Val His Trp Tyr Pro Gly Tyr Gly Ala Gly Asp Asn Tyr Ser Val Leu
        275                 280                 285

Gln Gln Gln Trp Asp Thr Asn Ile Lys Pro Cys Ala Asp Asn Tyr Pro
    290                 295                 300
```

```
Ile Asn Ile Thr Glu Thr Thr Trp Phe Lys Arg Leu Pro Gly Asp Ser
305                 310                 315                 320

Asp Tyr Trp Asn Leu Phe Asn Gly Ser Ser Glu Gly Phe Gly Lys Asn
            325                 330                 335

Thr Lys Ala Ile Phe Thr Ala Ala Gly Asn Ala Ser Ile Ala Val His
        340                 345                 350

Met Asn Gly Phe Leu Leu Ala Pro Gly Ala Arg Ser Ser Phe Ala Asp
    355                 360                 365

Pro Thr Ala Gly Leu Leu Tyr Asp Gly Asn Thr Ala Arg Asp Gly Met
370                 375                 380

Ala Arg Phe Ile Phe Glu Trp Tyr Tyr Glu Arg Ala Gln Phe Leu Pro
385                 390                 395                 400

Trp Asn Gly Ile Trp Asn Gly Leu Phe Thr Gly Ser Thr Tyr Lys Phe
            405                 410                 415

Val Asn Arg Ala Thr Gly Lys Asn Met Asp Val Pro Gly Gly Gln Asn
        420                 425                 430

Asn Asn Asn Leu Gln Leu Asn Gln Trp Thr Asp Asn Gly Ala Thr Ala
    435                 440                 445

Gln Arg Trp Val Val Asp Asp Met Gly Thr Phe Asn Asn Ile Tyr Arg
450                 455                 460

Met Lys Ser Val Ser Ser Ser Asp Gly Lys Val Met Asp Val Arg Asn
465                 470                 475                 480

Gly Thr Lys Asn Asn Gly Glu Ala Ile Gln Leu Met Gln Asp Phe Ser
            485                 490                 495

Asn Thr Ala Gln Arg Phe Arg Ile Ile Arg Leu Ser Asn Gly Tyr Trp
        500                 505                 510

Ser Ile Ile Asn Val Asn Ser Asn Lys Ala Val Glu Val Ala Gly Gly
    515                 520                 525

Ala Ser His Asp Gly Ala Leu Leu Gln Gln Asn Met Tyr Arg Gly Asp
530                 535                 540

His His Gln Gln Trp Gln Leu Val Gln Ile Gln
545                 550                 555

<210> SEQ ID NO 3
<211> LENGTH: 585
<212> TYPE: PRT
<213> ORGANISM: Chryseobacterium sp-10696

<400> SEQUENCE: 3

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala His His His His His
            20                  25                  30

His Pro Arg Asp Glu Lys Asn Leu Leu Glu Asp Pro Ser Asn Leu
        35                  40                  45

Ser Ala Gly Ala Ser Ala Arg Ala Leu Ala Ala Thr Pro Met Leu His
    50                  55                  60

Val Gly Gly Arg Tyr Leu Lys Asp Pro Cys Asp Asn Val Val Leu
65                  70                  75                  80

His Gly Val Ala Ile Thr Pro Ser Pro Trp Phe Asn Gly Cys Gln Tyr
            85                  90                  95

Gly Ala Asn Ser Gly Tyr Cys Thr Trp Asp Asn Tyr Asn Val Gln Gly
        100                 105                 110

Ala Leu Asn Tyr Asn Lys Ala Val Met Asn Lys Leu Thr Ser Ala Ala
    115                 120                 125
```

```
Asp Gly Trp Tyr Leu Asn Tyr Ile Arg Leu His Ile Asp Pro Tyr Trp
130                 135                 140

Thr Asn Asp Pro Gly Pro Ala Ile Pro Glu Asn Asp Ile Ser Arg Phe
145                 150                 155                 160

Asn Tyr Asn Arg Leu Val Thr Tyr Thr Asp Gln Val Ile Ile Pro Leu
                165                 170                 175

Ile Asn His Ala Arg Ser Leu Gly Met Tyr Val Ile Leu Arg Pro Pro
            180                 185                 190

Gly Val Cys Pro Asn Arg Ile Ala Val Asn Asp Ala Tyr His Ser Tyr
        195                 200                 205

Leu Lys Thr Val Trp Thr Phe Leu Ser Gln His Pro Gly Leu Lys Asn
210                 215                 220

Ala Asp Asn Val Met Phe Glu Leu Ala Asn Glu Pro Val Glu Ile Leu
225                 230                 235                 240

Gly Thr Asn Gly Thr Trp Gly Ser Thr Gly Asn Glu His Phe Ala Ala
                245                 250                 255

Leu Lys Asn Phe Phe Gln Pro Leu Val Asn Ile Ile Arg Asn Asn Gly
            260                 265                 270

Ala Asn Asn Val Cys Trp Ile Pro Gly Thr Gly Trp Gln Ser His Tyr
        275                 280                 285

Gln Gly Tyr Val Asn Asn Gln Ile Thr Gly Gly Asn Ile Gly Tyr Ala
290                 295                 300

Val His Ile Tyr Pro Ala Tyr Trp Gly Gly Leu Ser Asn Tyr Gln Ala
305                 310                 315                 320

Phe Gln Asn Ala Trp Asn Ile Asn Val Lys Pro Ile Ala Asp Ile Ala
                325                 330                 335

Pro Ile Ala Ile Thr Glu Thr Asp Trp Ala Pro Gln Gly Tyr Gly Thr
            340                 345                 350

Phe Gly Ile Gly Thr Thr Gly Thr Ala Gly Gly Ser Gly Phe Gly Ala
        355                 360                 365

Asn Leu Lys Tyr Ile Val Asp Gln Ser Gly Asn Val Ser Trp Asn Val
370                 375                 380

Leu Ala Pro Asp Asn Leu Leu His Lys Gly Asp Pro Asn Ala Gly Thr
385                 390                 395                 400

Ala Tyr Asn Asn Asp Trp Glu Ala Cys Ala Ala Pro Val Lys Gln Trp
                405                 410                 415

Phe Gln Gln Tyr Ala Ser Ser Asn Tyr Pro Val Gly Asn Cys Asn Thr
            420                 425                 430

Thr Ser Ser Leu Val Asn Asn Gly Ile Tyr Glu Ile Glu Phe Gln Thr
        435                 440                 445

Asp Ala Asn Lys Val Val Asp Leu Lys Ser Gly Glu Asp Ala Asn Gly
450                 455                 460

Ala Val Leu Arg Pro Trp Thr Arg Asn Gly Ala Ala Ala Gln Arg Trp
465                 470                 475                 480

Val Ala Ile Asp Ala Gly Asn Gly Tyr Trp Arg Phe Val Ser Lys Ala
                485                 490                 495

Ser Ala Thr Asn Arg Cys Ile Asp Leu Ala Ser Asn Ser Asn Thr Leu
            500                 505                 510

Gly Thr Ser Ile Arg Leu Trp Gln Asn Tyr Gly Asn Asp Ala Gln Ala
        515                 520                 525

Trp Gln Val Val Ala Val Ser Asn Gly Tyr Tyr Lys Ile Leu Ser Lys
530                 535                 540
```

```
Val Asp Pro Thr Arg Gly Trp Asp Ile Pro Asn Cys Thr Met Asp Gly
545                 550                 555                 560

Asn Ser Asn Leu His Leu Trp Asp Tyr Tyr Gly Thr Ser Cys Gln Leu
                565                 570                 575

Phe Lys Phe Lys Tyr Ile Gly Met Asn
                580                 585

<210> SEQ ID NO 4
<211> LENGTH: 391
<212> TYPE: PRT
<213> ORGANISM: Bacillus subtilis

<400> SEQUENCE: 4

Ala Ala Ser Asp Val Thr Val Asn Val Ser Ala Glu Lys Gln Val Ile
1               5                   10                  15

Arg Gly Phe Gly Gly Met Asn His Pro Ala Trp Ala Gly Asp Leu Thr
            20                  25                  30

Ala Ala Gln Arg Glu Thr Ala Phe Gly Asn Gly Gln Asn Gln Leu Gly
        35                  40                  45

Phe Ser Ile Leu Arg Ile His Val Asp Glu Asn Arg Asn Asn Trp Tyr
    50                  55                  60

Lys Glu Val Glu Thr Ala Lys Ser Ala Val Lys His Gly Ala Ile Val
65                  70                  75                  80

Phe Ala Ser Pro Trp Asn Pro Pro Ser Asp Met Val Glu Thr Phe Asn
                85                  90                  95

Arg Asn Gly Asp Thr Ser Ala Lys Arg Leu Lys Tyr Asn Lys Tyr Ala
            100                 105                 110

Ala Tyr Ala Gln His Leu Asn Asp Phe Val Thr Phe Met Lys Asn Asn
        115                 120                 125

Gly Val Asn Leu Tyr Ala Ile Ser Val Gln Asn Glu Pro Asp Tyr Ala
    130                 135                 140

His Glu Trp Thr Trp Trp Thr Pro Gln Glu Ile Leu Arg Phe Met Arg
145                 150                 155                 160

Glu Asn Ala Gly Ser Ile Asn Ala Arg Val Ile Ala Pro Glu Ser Phe
                165                 170                 175

Gln Tyr Leu Lys Asn Leu Ser Asp Pro Ile Leu Asn Asp Pro Gln Ala
            180                 185                 190

Leu Ala Asn Met Asp Ile Leu Gly Thr His Leu Tyr Gly Thr Gln Val
        195                 200                 205

Ser Gln Phe Pro Tyr Pro Leu Phe Lys Gln Lys Gly Ala Gly Lys Asp
    210                 215                 220

Leu Trp Met Thr Glu Val Tyr Tyr Pro Asn Ser Asp Thr Asn Ser Ala
225                 230                 235                 240

Asp Arg Trp Pro Glu Ala Leu Asp Val Ser Gln His Ile His Asn Ala
                245                 250                 255

Met Val Glu Gly Asp Phe Gln Ala Tyr Val Trp Trp Tyr Ile Arg Arg
            260                 265                 270

Ser Tyr Gly Pro Met Lys Glu Asp Gly Thr Ile Ser Lys Arg Gly Tyr
        275                 280                 285

Asn Met Ala His Phe Ser Lys Phe Val Arg Pro Gly Tyr Val Arg Ile
    290                 295                 300

Asp Ala Thr Lys Asn Pro Asn Ala Asn Val Tyr Val Ser Ala Tyr Lys
305                 310                 315                 320

Gly Asp Asn Lys Val Val Ile Val Ala Ile Asn Lys Ser Asn Thr Gly
                325                 330                 335
```

```
Val Asn Gln Asn Phe Val Leu Gln Asn Gly Ser Ala Ser Asn Val Ser
            340                 345                 350

Arg Trp Ile Thr Ser Ser Ser Asn Leu Gln Pro Gly Thr Asn Leu
        355                 360                 365

Thr Val Ser Gly Asn His Phe Trp Ala His Leu Pro Ala Gln Ser Val
    370                 375                 380

Thr Thr Phe Val Val Asn Arg
385                 390

<210> SEQ ID NO 5
<211> LENGTH: 417
<212> TYPE: PRT
<213> ORGANISM: Bacillus subtilis

<400> SEQUENCE: 5

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Ser Asp Val Thr
            20                  25                  30

Val Asn Val Ser Ala Glu Lys Gln Val Ile Arg Gly Phe Gly Gly Met
        35                  40                  45

Asn Trp Pro Ala Trp Ala Gly Asp Leu Thr Ala Ala Gln Arg Glu Thr
    50                  55                  60

Ala Phe Gly Asn Gly Gln Asn Gln Leu Gly Phe Ser Ile Leu Arg Ile
65                  70                  75                  80

His Val Asp Glu Asn Arg Asn Asn Trp Tyr Lys Glu Val Glu Thr Ala
                85                  90                  95

Lys Ser Ala Leu Lys Leu Gly Ala Ile Val Phe Ala Ser Pro Trp Asn
            100                 105                 110

Pro Pro Ser Asp Met Val Glu Thr Phe Asn Arg Asn Gly Asp Thr Ser
        115                 120                 125

Ala Lys Arg Leu Lys Tyr Asn Lys Tyr Ala Ala Tyr Ala Gln His Leu
    130                 135                 140

Asn Asp Phe Val Thr Phe Met Lys Asn Asn Gly Val Asn Leu Tyr Ala
145                 150                 155                 160

Ile Ser Val Gln Asn Glu Pro Asp Tyr Ala His Glu Trp Thr Trp Trp
                165                 170                 175

Thr Pro Gln Glu Met Leu Arg Phe Met Arg Glu Asn Ala Gly Ser Ile
            180                 185                 190

Asn Ala Arg Val Ile Ala Pro Glu Ser Phe Gln Tyr Leu Lys Asn Leu
        195                 200                 205

Ser Asp Pro Ile Leu Asn Asp Pro Gln Ala Leu Ala Asn Met Asp Ile
    210                 215                 220

Leu Gly Thr His Leu Tyr Gly Thr Gln Leu Ser Gln Phe Pro Tyr Pro
225                 230                 235                 240

Leu Phe Lys Gln Lys Gly Ala Gly Lys Asp Leu Trp Met Thr Glu Val
                245                 250                 255

Tyr Tyr Pro Asn Ser Asp Thr Asn Ser Ala Asp Arg Trp Pro Glu Ala
            260                 265                 270

Leu Asp Val Ser Gln His Ile His Asn Ala Met Val Glu Gly Asp Phe
        275                 280                 285

Gln Ala Tyr Val Trp Trp Tyr Ile Arg Arg Ser Tyr Gly Pro Met Lys
    290                 295                 300

Glu Asp Gly Thr Ile Ser Lys Arg Gly Tyr Asn Met Ala His Phe Ser
```

```
                305                 310                 315                 320
Lys Phe Val Arg Pro Gly Tyr Val Arg Ile Asp Ala Thr Lys Asn Pro
                    325                 330                 335

Asn Ala Asn Val Tyr Val Ser Ala Tyr Lys Gly Asp Asn Lys Val Val
                340                 345                 350

Ile Val Ala Ile Asn Lys Ser Asn Thr Gly Val Asn Gln Asn Phe Val
            355                 360                 365

Leu Gln Asn Gly Ser Ala Ser Asn Val Ser Arg Trp Ile Thr Ser Ser
370                 375                 380

Ser Ser Asn Leu Gln Pro Gly Thr Asn Leu Thr Val Ser Gly Asn His
385                 390                 395                 400

Phe Trp Ala His Leu Pro Ala Gln Ser Val Thr Thr Phe Val Val Asn
                    405                 410                 415

Arg

<210> SEQ ID NO 6
<211> LENGTH: 417
<212> TYPE: PRT
<213> ORGANISM: Bacillus subtilis

<400> SEQUENCE: 6

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Ala Ser Asp Val Thr
                20                  25                  30

Val Asn Val Ser Ala Glu Lys Gln Val Ile Arg Gly Phe Gly Gly Met
            35                  40                  45

Asn Trp Pro Ala Trp Ala Gly Asp Leu Thr Ala Ala Gln Arg Glu Thr
50                  55                  60

Ala Phe Gly Asn Gly Gln Asn Gln Leu Gly Phe Ser Ile Leu Arg Ile
65                  70                  75                  80

His Val Asp Glu Asn Arg Asn Asn Trp Tyr Lys Glu Val Glu Thr Ala
                85                  90                  95

Lys Ser Ala Val Leu Leu Gly Ala Ile Val Phe Ala Ser Pro Trp Asn
                    100                 105                 110

Pro Pro Ser Asp Met Val Glu Thr Phe Asn Arg Asn Gly Asp Thr Ser
                115                 120                 125

Ala Lys Arg Leu Lys Tyr Asn Lys Tyr Ala Ala Tyr Ala Gln His Leu
            130                 135                 140

Asn Asp Phe Val Thr Phe Met Lys Asn Asn Gly Val Asn Leu Tyr Ala
145                 150                 155                 160

Ile Ser Val Gln Asn Glu Pro Asp Tyr Ala His Glu Trp Thr Trp Trp
                165                 170                 175

Thr Pro Gln Glu Met Leu Arg Phe Met Arg Glu Asn Ala Gly Ser Ile
                    180                 185                 190

Asn Ala Arg Val Ile Ala Pro Glu Ser Phe Gln Tyr Leu Lys Asn Leu
                195                 200                 205

Ser Asp Pro Ile Leu Asn Asp Pro Gln Ala Leu Ala Asn Met Asp Ile
            210                 215                 220

Leu Gly Thr His Leu Tyr Gly Thr Gln Leu Ser Gln Phe Pro Tyr Pro
225                 230                 235                 240

Leu Phe Lys Gln Lys Gly Ala Gly Lys Asp Leu Trp Met Thr Glu Val
                245                 250                 255

Tyr Tyr Pro Asn Ser Asp Thr Asn Ser Ala Asp Arg Trp Pro Glu Ala
```

```
                    260                 265                 270
Leu Asp Val Ser Gln His Ile His Asn Ala Met Val Glu Gly Asp Phe
            275                 280                 285

Gln Ala Tyr Val Trp Tyr Ile Arg Arg Ser Tyr Gly Pro Met Lys
        290                 295                 300

Glu Asp Gly Thr Ile Ser Lys Arg Gly Tyr Asn Met Ala His Phe Ser
305                 310                 315                 320

Lys Phe Val Arg Pro Gly Tyr Val Arg Ile Asp Ala Thr Lys Asn Pro
                325                 330                 335

Asn Ala Asn Val Tyr Val Ser Ala Tyr Lys Gly Asp Asn Lys Val Val
            340                 345                 350

Ile Val Ala Ile Asn Lys Ser Asn Thr Gly Val Asn Gln Asn Phe Val
        355                 360                 365

Leu Gln Asn Gly Ser Ala Ser Asn Val Ser Arg Trp Ile Thr Ser Ser
    370                 375                 380

Ser Ser Asn Leu Gln Pro Gly Thr Asn Leu Thr Val Ser Gly Asn His
385                 390                 395                 400

Phe Trp Ala His Leu Pro Ala Gln Ser Val Thr Thr Phe Val Val Asn
                405                 410                 415

Arg

<210> SEQ ID NO 7
<211> LENGTH: 417
<212> TYPE: PRT
<213> ORGANISM: Bacillus subtilis

<400> SEQUENCE: 7

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Ala Ser Asp Val Thr
            20                  25                  30

Val Asn Val Ser Ala Glu Lys Gln Val Ile Arg Gly Phe Gly Gly Met
        35                  40                  45

Asn His Pro Ala Trp Ala Gly Asp Leu Thr Ala Ala Gln Arg Glu Thr
    50                  55                  60

Ala Phe Gly Asn Gly Gln Asn Gln Leu Gly Phe Ser Ile Leu Arg Ile
65                  70                  75                  80

His Val Asp Glu Asn Arg Asn Asn Trp Tyr Lys Glu Val Glu Thr Ala
                85                  90                  95

Lys Ser Ala Val Lys His Gly Ala Ile Val Phe Ala Ser Pro Trp Asn
            100                 105                 110

Pro Pro Ser Asp Met Val Glu Thr Phe Asn Arg Asn Gly Asp Thr Ser
        115                 120                 125

Ala Lys Arg Leu Lys Tyr Asn Lys Tyr Ala Ala Tyr Ala Gln His Leu
    130                 135                 140

Asn Asp Phe Val Thr Phe Met Lys Asn Asn Gly Val Asn Leu Tyr Ala
145                 150                 155                 160

Ile Ser Val Gln Asn Glu Pro Asp Tyr Ala His Glu Trp Thr Trp Trp
                165                 170                 175

Thr Pro Gln Glu Ile Leu Arg Phe Met Arg Glu Asn Ala Gly Ser Ile
            180                 185                 190

Asn Ala Arg Val Ile Ala Pro Glu Ser Phe Gln Tyr Leu Lys Asn Leu
        195                 200                 205

Ser Asp Pro Ile Leu Asn Asp Pro Gln Ala Leu Ala Asn Met Asp Ile
```

```
                210                 215                 220
Leu Gly Thr His Leu Tyr Gly Thr Gln Val Ser Gln Phe Pro Tyr Pro
225                 230                 235                 240

Leu Phe Lys Gln Lys Gly Ala Gly Lys Asp Leu Trp Met Thr Glu Val
                245                 250                 255

Tyr Tyr Pro Asn Ser Asp Thr Asn Ser Ala Asp Arg Trp Pro Glu Ala
                260                 265                 270

Leu Asp Val Ser Gln His Ile His Asn Ala Met Val Glu Gly Asp Phe
                275                 280                 285

Gln Ala Tyr Val Trp Trp Tyr Ile Arg Arg Ser Tyr Gly Pro Met Lys
290                 295                 300

Glu Asp Gly Thr Ile Ser Lys Arg Gly Tyr Asn Met Ala His Phe Ser
305                 310                 315                 320

Lys Phe Val Arg Pro Gly Tyr Val Arg Ile Asp Ala Thr Lys Asn Pro
                325                 330                 335

Asn Ala Asn Val Tyr Val Ser Ala Tyr Lys Gly Asp Asn Lys Val Val
                340                 345                 350

Ile Val Ala Ile Asn Lys Ser Asn Thr Gly Val Asn Gln Asn Phe Val
                355                 360                 365

Leu Gln Asn Gly Ser Ala Ser Asn Val Ser Arg Trp Ile Thr Ser Ser
370                 375                 380

Ser Ser Asn Leu Gln Pro Gly Thr Asn Leu Thr Val Ser Gly Asn His
385                 390                 395                 400

Phe Trp Ala His Leu Pro Ala Gln Ser Val Thr Thr Phe Val Val Asn
                405                 410                 415

Arg

<210> SEQ ID NO 8
<211> LENGTH: 557
<212> TYPE: PRT
<213> ORGANISM: Chrysobacterium sp.

<400> SEQUENCE: 8

Met His His His His His Asp Glu Lys Asn Leu Leu Glu Asp Pro
1               5                   10                  15

Asp Ser Asn Leu Ser Ala Gly Ala Ser Ala Arg Ala Leu Ala Ala Thr
                20                  25                  30

Pro Met Leu His Val Gly Gly Arg Tyr Leu Lys Asp Pro Cys Asp Asn
                35                  40                  45

Asn Val Val Leu His Gly Val Ala Ile Thr Pro Ser Pro Trp Phe Asn
                50                  55                  60

Gly Cys Gln Tyr Gly Ala Asn Ser Gly Tyr Cys Thr Trp Asp Asn Tyr
65                  70                  75                  80

Asn Val Gln Gly Ala Leu Asn Tyr Asn Lys Ala Val Met Asn Lys Leu
                85                  90                  95

Thr Ser Ala Ala Asp Gly Trp Tyr Leu Asn Tyr Ile Arg Leu His Ile
                100                 105                 110

Asp Pro Tyr Trp Thr Asn Asp Pro Gly Pro Ala Ile Pro Glu Asn Asp
                115                 120                 125

Ile Ser Arg Phe Asn Tyr Asn Arg Leu Val Thr Tyr Thr Asp Gln Val
                130                 135                 140

Ile Ile Pro Leu Ile Asn His Ala Arg Ser Leu Gly Met Tyr Val Ile
145                 150                 155                 160

Leu Arg Pro Pro Gly Val Cys Pro Asn Arg Ile Ala Val Asn Asp Ala
```

```
                165                 170                 175
Tyr His Ser Tyr Leu Lys Thr Val Trp Thr Phe Leu Ser Gln His Pro
            180                 185                 190
Gly Leu Lys Asn Ala Asp Asn Val Met Phe Glu Leu Ala Asn Glu Pro
            195                 200                 205
Val Glu Ile Leu Gly Thr Asn Gly Thr Trp Gly Ser Thr Gly Asn Glu
            210                 215                 220
His Phe Ala Ala Leu Lys Asn Phe Phe Gln Pro Leu Val Asn Ile Ile
225                 230                 235                 240
Arg Asn Asn Gly Ala Asn Asn Val Cys Trp Ile Pro Gly Thr Gly Trp
                245                 250                 255
Gln Ser His Tyr Gln Gly Tyr Val Asn Asn Gln Ile Thr Gly Gly Asn
                260                 265                 270
Ile Gly Tyr Ala Val His Ile Tyr Pro Ala Tyr Trp Gly Gly Leu Ser
                275                 280                 285
Asn Tyr Gln Ala Phe Gln Asn Ala Trp Asn Ile Asn Val Lys Pro Ile
            290                 295                 300
Ala Asp Ile Ala Pro Ile Ala Ile Thr Glu Thr Asp Trp Ala Pro Gln
305                 310                 315                 320
Gly Tyr Gly Thr Phe Gly Ile Gly Thr Thr Gly Thr Ala Gly Gly Ser
                325                 330                 335
Gly Phe Gly Ala Asn Leu Lys Tyr Ile Val Asp Gln Ser Gly Asn Val
            340                 345                 350
Ser Trp Asn Val Leu Ala Pro Asp Asn Leu His Lys Gly Asp Pro
            355                 360                 365
Asn Ala Gly Thr Ala Tyr Asn Asn Asp Trp Glu Ala Cys Ala Ala Pro
            370                 375                 380
Val Lys Gln Trp Phe Gln Gln Tyr Ala Ser Ser Asn Tyr Pro Val Gly
385                 390                 395                 400
Asn Cys Asn Thr Thr Ser Ser Leu Val Asn Asn Gly Ile Tyr Glu Ile
                405                 410                 415
Glu Phe Gln Thr Asp Ala Asn Lys Val Val Asp Leu Lys Ser Gly Glu
            420                 425                 430
Asp Ala Asn Gly Ala Val Leu Arg Pro Trp Thr Arg Asn Gly Ala Ala
            435                 440                 445
Ala Gln Arg Trp Val Ala Ile Asp Ala Gly Asn Gly Tyr Trp Arg Phe
            450                 455                 460
Val Ser Lys Ala Ser Ala Thr Asn Arg Cys Ile Asp Leu Ala Ser Asn
465                 470                 475                 480
Ser Asn Thr Leu Gly Thr Ser Ile Arg Leu Trp Gln Asn Tyr Gly Asn
                485                 490                 495
Asp Ala Gln Ala Trp Gln Val Val Ala Val Ser Asn Gly Tyr Tyr Lys
            500                 505                 510
Ile Leu Ser Lys Val Asp Pro Thr Arg Gly Trp Asp Ile Pro Asn Cys
            515                 520                 525
Thr Met Asp Gly Asn Ser Asn Leu His Leu Trp Asp Tyr Tyr Gly Thr
            530                 535                 540
Ser Cys Gln Leu Phe Lys Phe Lys Tyr Ile Gly Met Asn
545                 550                 555

<210> SEQ ID NO 9
<211> LENGTH: 2731
<212> TYPE: DNA
<213> ORGANISM: Sphingobacterium sp.
```

```
<220> FEATURE:
<221> NAME/KEY: CDS
<222> LOCATION: (501)..(2231)

<400> SEQUENCE: 9
tgactatggc ttggaaggca gtggcaacaa atgtaaaggg ctcatcgcct atgtcggcta      60
catcgaaggc aaaggggcca agtggatgg aatcggcacc cagatgcaca tcgatatcaa     120
taccagtaaa gaccaaatcg tcagcatgtt caatctattg ccgcaacag gcaagctgat     180 taaagtgtct gagctcgata tcggccttgg aagcggcata aagaccagca atgcaacagc     240
tgaaatgtat cagaaacagg ctgatttata caagtttgtc gttgagaaat acctcgagat     300
cattcccaag gataaacagt acggtatcac cctatggagc ccgttggata gtccagacca     360
ggagggttca ttctggcgac gtggagagcc catcggctta tggaccgaag gatttgtccg     420
aaagccagcc tatcaggctg ttgctgaggc attgtcagct aaaaaataag atcattaatc     480 acccttaaa tatgtaaatt atg aga aca aac aac atg tgg tta ttg ctg atc     533
                    Met Arg Thr Asn Asn Met Trp Leu Leu Leu Ile
                     1               5                  10 ttt tta tta gct att ttt tcc agc tgc tcg cgg ctg gaa gaa aaa aca      581
Phe Leu Leu Ala Ile Phe Ser Ser Cys Ser Arg Leu Glu Glu Lys Thr
            15                  20                  25 ttg acc agc gaa tcc gaa aga agt ctt aaa tcc aat gtt tcc gcg caa      629
Leu Thr Ser Glu Ser Glu Arg Ser Leu Lys Ser Asn Val Ser Ala Gln
    30                  35                  40 gcc gtt aca agc tgg ccg cgg cca acc ccg acc cta cat gtc gga ggc      677
Ala Val Thr Ser Trp Pro Arg Pro Thr Pro Thr Leu His Val Gly Gly
45                  50                  55 aag tac ctc aaa gat ccc tgc gac aat aat att gtc ctg cat ggg gta      725
Lys Tyr Leu Lys Asp Pro Cys Asp Asn Asn Ile Val Leu His Gly Val
60                  65                  70                  75 gcc att acg cca agc cct tgg ttc aat ggc tgt cag tat gga gcc aac      773
Ala Ile Thr Pro Ser Pro Trp Phe Asn Gly Cys Gln Tyr Gly Ala Asn
            80                  85                  90 tcg ggc tac tgc acc tgg gac aat tac aat gtg cag ggc gcg ctc aat      821
Ser Gly Tyr Cys Thr Trp Asp Asn Tyr Asn Val Gln Gly Ala Leu Asn
        95                  100                 105 tac aac aag gcg gtc atg gac aag ctc agc agc gcc gcc gac ggt tgg      869
Tyr Asn Lys Ala Val Met Asp Lys Leu Ser Ser Ala Ala Asp Gly Trp
    110                 115                 120 tac ctc aat tat atc cgt ctg cat att gat cct tat tgg acc aat gat      917
Tyr Leu Asn Tyr Ile Arg Leu His Ile Asp Pro Tyr Trp Thr Asn Asp
125                 130                 135 cca ggt gca ccc att ccc gaa gac gat atc tca cgg ttc aac tac aat      965
Pro Gly Ala Pro Ile Pro Glu Asp Asp Ile Ser Arg Phe Asn Tyr Asn
140                 145                 150                 155 cgg ctg gtt acc tac acc gac cag gtc att gtc ccc tta atc aat cat     1013
Arg Leu Val Thr Tyr Thr Asp Gln Val Ile Val Pro Leu Ile Asn His
            160                 165                 170 gcc cgc agc cgc ggt atg tat gtc atc ttg cgt cct cca ggt gta tgt     1061
Ala Arg Ser Arg Gly Met Tyr Val Ile Leu Arg Pro Pro Gly Val Cys
        175                 180                 185 ccg cac cgt atc gcc gtc aat gat gcc tat cat acc tat ctc aag acc     1109
Pro His Arg Ile Ala Val Asn Asp Ala Tyr His Thr Tyr Leu Lys Thr
    190                 195                 200 gta tgg acc ttt ctg tcg cag cac act gcc ctg aaa aat gca gac aat     1157
Val Trp Thr Phe Leu Ser Gln His Thr Ala Leu Lys Asn Ala Asp Asn
205                 210                 215 gtg atg ttt gaa ttg gct aac gag cct gtt gaa atc ctt ggg acg aac     1205
```

|       |     |     |     |     |     |     |     |     |     |     |     |     |     |     |     |      |
|-------|-----|-----|-----|-----|-----|-----|-----|-----|-----|-----|-----|-----|-----|-----|-----|------|
|       | Val | Met | Phe | Glu | Leu | Ala | Asn | Glu | Pro | Val | Glu | Ile | Leu | Gly | Thr | Asn  |
|       | 220 |     |     |     | 225 |     |     |     |     | 230 |     |     |     |     | 235 |      |
| ggt   | act | tgg | gga | atg | acg | gga | aat | gaa | cat | ttt | gct | gcg | ctg | aaa | aat | 1253 |
| Gly   | Thr | Trp | Gly | Met | Thr | Gly | Asn | Glu | His | Phe | Ala | Ala | Leu | Lys | Asn |      |
|       |     |     |     | 240 |     |     |     |     | 245 |     |     |     |     | 250 |     |      |
| ttc   | ttt | cag | ccc | tta | gtc | aat | atc | atc | cgt | aac | aac | ggt | gcc | aac | aac | 1301 |
| Phe   | Phe | Gln | Pro | Leu | Val | Asn | Ile | Ile | Arg | Asn | Asn | Gly | Ala | Asn | Asn |      |
|       |     |     | 255 |     |     |     |     | 260 |     |     |     |     | 265 |     |     |      |
| gtc   | tgc | tgg | ata | ccc | ggt | acc | ggt | tgg | caa | tcc | cat | tac | cag | ggt | tat | 1349 |
| Val   | Cys | Trp | Ile | Pro | Gly | Thr | Gly | Trp | Gln | Ser | His | Tyr | Gln | Gly | Tyr |      |
|       |     | 270 |     |     |     |     | 275 |     |     |     |     | 280 |     |     |     |      |
| gtc   | act | aat | cag | att | acc | ggc | gga | aat | atc | ggc | tac | gcc | gta | cat | atc | 1397 |
| Val   | Thr | Asn | Gln | Ile | Thr | Gly | Gly | Asn | Ile | Gly | Tyr | Ala | Val | His | Ile |      |
|       | 285 |     |     |     |     | 290 |     |     |     |     | 295 |     |     |     |     |      |
| tat   | ccg | ggt | tat | tgg | ggc | ggt | gtc | aat | acc | tat | caa | gct | ttc | caa | aat | 1445 |
| Tyr   | Pro | Gly | Tyr | Trp | Gly | Gly | Val | Asn | Thr | Tyr | Gln | Ala | Phe | Gln | Asn |      |
| 300   |     |     |     |     | 305 |     |     |     |     | 310 |     |     |     |     | 315 |      |
| gcc   | tgg | aat | acc | aat | gtc | aaa | cct | att | gct | gac | att | gcg | cca | atc | gct | 1493 |
| Ala   | Trp | Asn | Thr | Asn | Val | Lys | Pro | Ile | Ala | Asp | Ile | Ala | Pro | Ile | Ala |      |
|       |     |     | 320 |     |     |     |     | 325 |     |     |     |     | 330 |     |     |      |
| att   | aca | gag | acc | gac | tgg | gct | cca | cag | gga | tat | ggt | act | ttc | ggc | aca | 1541 |
| Ile   | Thr | Glu | Thr | Asp | Trp | Ala | Pro | Gln | Gly | Tyr | Gly | Thr | Phe | Gly | Thr |      |
|       |     |     | 335 |     |     |     |     | 340 |     |     |     |     | 345 |     |     |      |
| gga   | tct | acg | ggc | acc | gct | ggt | ggt | aat | ggt | ttt | ggt | gca | aat | ttg | aaa | 1589 |
| Gly   | Ser | Thr | Gly | Thr | Ala | Gly | Gly | Asn | Gly | Phe | Gly | Ala | Asn | Leu | Lys |      |
|       |     | 350 |     |     |     |     | 355 |     |     |     |     | 360 |     |     |     |      |
| tat   | atc | gtc | gat | cag | tct | ggc | aat | gtc | agc | tgg | aac | ctc | ctt | act | ccc | 1637 |
| Tyr   | Ile | Val | Asp | Gln | Ser | Gly | Asn | Val | Ser | Trp | Asn | Leu | Leu | Thr | Pro |      |
|       | 365 |     |     |     |     | 370 |     |     |     |     | 375 |     |     |     |     |      |
| gat   | gac | ctg | ctc | cat | aaa | ggg | gac | ccc | aat | gcc | ggc | acc | gcc | ttt | aat | 1685 |
| Asp   | Asp | Leu | Leu | His | Lys | Gly | Asp | Pro | Asn | Ala | Gly | Thr | Ala | Phe | Asn |      |
| 380   |     |     |     |     | 385 |     |     |     |     | 390 |     |     |     |     | 395 |      |
| aac   | gat | tgg | gag | gcc | tgc | gct | gca | ccg | agc | aaa | caa | tgg | ttt | cag | caa | 1733 |
| Asn   | Asp | Trp | Glu | Ala | Cys | Ala | Ala | Pro | Ser | Lys | Gln | Trp | Phe | Gln | Gln |      |
|       |     |     |     | 400 |     |     |     |     | 405 |     |     |     |     | 410 |     |      |
| tat   | gcc | gcc | tac | aat | tac | ccc | atg | tct | aac | tgc | acc | gtc | acc | agc | ttg | 1781 |
| Tyr   | Ala | Ala | Tyr | Asn | Tyr | Pro | Met | Ser | Asn | Cys | Thr | Val | Thr | Ser | Leu |      |
|       |     |     | 415 |     |     |     |     | 420 |     |     |     |     | 425 |     |     |      |
| gtg   | aac | aat | ggg | att | tac | gaa | att | gaa | ttt | cag | acc | gat | gcc | aac | aaa | 1829 |
| Val   | Asn | Asn | Gly | Ile | Tyr | Glu | Ile | Glu | Phe | Gln | Thr | Asp | Ala | Asn | Lys |      |
|       |     | 430 |     |     |     |     | 435 |     |     |     |     | 440 |     |     |     |      |
| gtc   | ctt | gat | ttg | aaa | tca | ggg | gaa | gat | gcc | aac | ggt | gca | gca | ctc | aga | 1877 |
| Val   | Leu | Asp | Leu | Lys | Ser | Gly | Glu | Asp | Ala | Asn | Gly | Ala | Ala | Leu | Arg |      |
|       | 445 |     |     |     |     | 450 |     |     |     |     | 455 |     |     |     |     |      |
| ccc   | tgg | acc | cga | aat | ggt | gca | aac | gca | cag | cgc | tgg | gta | gcc | atc | gat | 1925 |
| Pro   | Trp | Thr | Arg | Asn | Gly | Ala | Asn | Ala | Gln | Arg | Trp | Val | Ala | Ile | Asp |      |
| 460   |     |     |     |     | 465 |     |     |     |     | 470 |     |     |     |     | 475 |      |
| gca   | ggc | aat | ggt | tac | tgg | cgc | ttt | gtc | tcc | aaa | gca | agc | gca | agc | agt | 1973 |
| Ala   | Gly | Asn | Gly | Tyr | Trp | Arg | Phe | Val | Ser | Lys | Ala | Ser | Ala | Ser | Ser |      |
|       |     |     |     | 480 |     |     |     |     | 485 |     |     |     |     | 490 |     |      |
| cgt   | tgc | atc | gat | ctg | aca | agt | aac | agt | aat | gta | ctc | gga | act | gcg | atc | 2021 |
| Arg   | Cys | Ile | Asp | Leu | Thr | Ser | Asn | Ser | Asn | Val | Leu | Gly | Thr | Ala | Ile |      |
|       |     |     | 495 |     |     |     |     | 500 |     |     |     |     | 505 |     |     |      |
| cgg   | ctc | tgg | cag | aac | tat | ggc | aat | gat | gcg | cag | gcc | tgg | aag | gtt | aca | 2069 |
| Arg   | Leu | Trp | Gln | Asn | Tyr | Gly | Asn | Asp | Ala | Gln | Ala | Trp | Lys | Val | Thr |      |
|       |     | 510 |     |     |     |     | 515 |     |     |     |     | 520 |     |     |     |      |
| gct   | gta | gct | aat | ggc | tat | tac | aaa | att | acc | tca | aag | gta | gat | gcc | aca | 2117 |
| Ala   | Val | Ala | Asn | Gly | Tyr | Tyr | Lys | Ile | Thr | Ser | Lys | Val | Asp | Ala | Thr |      |
|       | 525 |     |     |     |     | 530 |     |     |     |     | 535 |     |     |     |     |      |

```
cgc ggt tgg gat gta ccc agc tgc acg atg gat ggc aac tcc aat ctg    2165
Arg Gly Trp Asp Val Pro Ser Cys Thr Met Asp Gly Asn Ser Asn Leu
540                 545                 550                 555 cag ctt tgg gat tac tat ggt aca tcc tgt cag ttg ttt aaa ttc aaa    2213
Gln Leu Trp Asp Tyr Tyr Gly Thr Ser Cys Gln Leu Phe Lys Phe Lys
                560                 565                 570 ttt ata gcg atg aac taa aggtcatctt ttcgcggtaa gctattctta           2261
Phe Ile Ala Met Asn
                575 ccgcgaaata gtttatttta atcacatgaa aaacttcacc atgcgacaaa cacaatttaa  2321 aatcctgtta atgatcttcc tactatgcgg tttttcaggt acagcagcgt tcgcccaaga  2381 caaaaacttc catatttacc tttgctttgg acaatccaat atggaagggc acggtaaatt  2441 cgaacctcag gataccatgg ccatcgaacg gttcaaggta ctatcggcag tagattgccc  2501 cgatttaggg cggcaatatg ccgatggtc gccggcccgg gcaccgctca cacgctgcca   2561 caccggactt acacctgcag attattttag ccgaacactt gtagaaaatc ttcccaaaaa  2621 tattgaggtc ggtgtcatca acgtttcagt aggtggctgt catattcaat tatttgatca  2681 ggacagcaca gcaagttatg ttgcaaagtc accggaatgg atgaaatcca             2731
```

<210> SEQ ID NO 10
<211> LENGTH: 576
<212> TYPE: PRT
<213> ORGANISM: Sphingobacterium sp.

<400> SEQUENCE: 10

```
Met Arg Thr Asn Asn Met Trp Leu Leu Leu Ile Phe Leu Leu Ala Ile
1               5                   10                  15

Phe Ser Ser Cys Ser Arg Leu Glu Glu Lys Thr Leu Thr Ser Glu Ser
                20                  25                  30

Glu Arg Ser Leu Lys Ser Asn Val Ser Ala Gln Ala Val Thr Ser Trp
            35                  40                  45

Pro Arg Pro Thr Pro Thr Leu His Val Gly Gly Lys Tyr Leu Lys Asp
        50                  55                  60

Pro Cys Asp Asn Asn Ile Val Leu His Gly Val Ala Ile Thr Pro Ser
65                  70                  75                  80

Pro Trp Phe Asn Gly Cys Gln Tyr Gly Ala Asn Ser Gly Tyr Cys Thr
                85                  90                  95

Trp Asp Asn Tyr Asn Val Gln Gly Ala Leu Asn Tyr Asn Lys Ala Val
                100                 105                 110

Met Asp Lys Leu Ser Ser Ala Ala Asp Gly Trp Tyr Leu Asn Tyr Ile
            115                 120                 125

Arg Leu His Ile Asp Pro Tyr Trp Thr Asn Asp Pro Gly Ala Pro Ile
        130                 135                 140

Pro Glu Asp Asp Ile Ser Arg Phe Asn Tyr Asn Arg Leu Val Thr Tyr
145                 150                 155                 160

Thr Asp Gln Val Ile Val Pro Leu Ile Asn His Ala Arg Ser Arg Gly
                165                 170                 175

Met Tyr Val Ile Leu Arg Pro Pro Gly Val Cys Pro His Arg Ile Ala
            180                 185                 190

Val Asn Asp Ala Tyr His Thr Tyr Leu Lys Thr Val Trp Thr Phe Leu
        195                 200                 205

Ser Gln His Thr Ala Leu Lys Asn Ala Asp Asn Val Met Phe Glu Leu
210                 215                 220

Ala Asn Glu Pro Val Glu Ile Leu Gly Thr Asn Gly Thr Trp Gly Met
```

|     |     |     |     | 225 |     |     |     |     | 230 |     |     |     |     | 235 |     |     |     |     | 240 |
| --- | --- | --- | --- | --- | --- | --- | --- | --- | --- | --- | --- | --- | --- | --- | --- | --- | --- | --- | --- |

Thr Gly Asn Glu His Phe Ala Ala Leu Lys Asn Phe Phe Gln Pro Leu
                            245                            250                            255

Val Asn Ile Ile Arg Asn Asn Gly Ala Asn Asn Val Cys Trp Ile Pro
                    260                            265                            270

Gly Thr Gly Trp Gln Ser His Tyr Gln Gly Tyr Val Thr Asn Gln Ile
               275                         280                          285

Thr Gly Gly Asn Ile Gly Tyr Ala Val His Ile Tyr Pro Gly Tyr Trp
          290                         295                            300

Gly Gly Val Asn Thr Tyr Gln Ala Phe Gln Asn Ala Trp Asn Thr Asn
305                            310                            315                            320

Val Lys Pro Ile Ala Asp Ile Ala Pro Ile Ala Ile Thr Glu Thr Asp
                          325                            330                            335

Trp Ala Pro Gln Gly Tyr Gly Thr Phe Gly Thr Gly Ser Thr Gly Thr
               340                         345                          350

Ala Gly Gly Asn Gly Phe Gly Ala Asn Leu Lys Tyr Ile Val Asp Gln
                    355                            360                          365

Ser Gly Asn Val Ser Trp Asn Leu Leu Thr Pro Asp Asp Leu Leu His
       370                          375                            380

Lys Gly Asp Pro Asn Ala Gly Thr Ala Phe Asn Asn Asp Trp Glu Ala
385                            390                            395                            400

Cys Ala Ala Pro Ser Lys Gln Trp Phe Gln Gln Tyr Ala Ala Tyr Asn
                    405                            410                          415

Tyr Pro Met Ser Asn Cys Thr Val Thr Ser Leu Val Asn Asn Gly Ile
               420                         425                          430

Tyr Glu Ile Glu Phe Gln Thr Asp Ala Asn Lys Val Leu Asp Leu Lys
          435                         440                            445

Ser Gly Glu Asp Ala Asn Gly Ala Ala Leu Arg Pro Trp Thr Arg Asn
               450                         455                          460

Gly Ala Asn Ala Gln Arg Trp Val Ala Ile Asp Ala Gly Asn Gly Tyr
465                            470                            475                            480

Trp Arg Phe Val Ser Lys Ala Ser Ala Ser Arg Cys Ile Asp Leu
                    485                            490                          495

Thr Ser Asn Ser Asn Val Leu Gly Thr Ala Ile Arg Leu Trp Gln Asn
                    500                            505                          510

Tyr Gly Asn Asp Ala Gln Ala Trp Lys Val Thr Ala Val Ala Asn Gly
               515                         520                          525

Tyr Tyr Lys Ile Thr Ser Lys Val Asp Ala Thr Arg Gly Trp Asp Val
          530                         535                            540

Pro Ser Cys Thr Met Asp Gly Asn Ser Asn Leu Gln Leu Trp Asp Tyr
545                            550                            555                            560

Tyr Gly Thr Ser Cys Gln Leu Phe Lys Phe Lys Phe Ile Ala Met Asn
               565                         570                          575

```
<210> SEQ ID NO 11
<211> LENGTH: 1698
<212> TYPE: DNA
<213> ORGANISM: Bacillus hemicellulosilyticus
<220> FEATURE:
<221> NAME/KEY: CDS
<222> LOCATION: (1)..(1698)

<400> SEQUENCE: 11 atg cgc gag gta ggt cgc atg acg aaa atg ctt ctt gtt gtt atg ttc      48
Met Arg Glu Val Gly Arg Met Thr Lys Met Leu Leu Val Val Met Phe
1               5                   10                  15
```

```
atc gtt ccg ctt ctt ctt tct ggc cat tct gcg gag gct tgg act gga    96
Ile Val Pro Leu Leu Leu Ser Gly His Ser Ala Glu Ala Trp Thr Gly
         20                  25                  30 atg cct atg gac aaa ctt cat gta agc ggc aac caa ctt gta aac agc   144
Met Pro Met Asp Lys Leu His Val Ser Gly Asn Gln Leu Val Asn Ser
     35                  40                  45 tct ggc caa act gta ctt ctt aac ggc tgg cac caa cct tct ggc tct   192
Ser Gly Gln Thr Val Leu Leu Asn Gly Trp His Gln Pro Ser Gly Ser
 50                  55                  60 tac tgg act tac cag ggc tca aac tac tat ctt gac cgc aac ggt ggc   240
Tyr Trp Thr Tyr Gln Gly Ser Asn Tyr Tyr Leu Asp Arg Asn Gly Gly
 65                  70                  75                  80 aac cgc cat gcc gct aac ctt gag tat ctt aaa gac atc agc gac act   288
Asn Arg His Ala Ala Asn Leu Glu Tyr Leu Lys Asp Ile Ser Asp Thr
                 85                  90                  95 ttc act gac aca tct ccg aaa tac ggc aac gac cac ggc tgg tac atg   336
Phe Thr Asp Thr Ser Pro Lys Tyr Gly Asn Asp His Gly Trp Tyr Met
            100                 105                 110 aac caa atc cgc ctt ttc atc gac cgc gag gac atg ggc gac gta gcg   384
Asn Gln Ile Arg Leu Phe Ile Asp Arg Glu Asp Met Gly Asp Val Ala
        115                 120                 125 gct ggc acg tat aac ttc gct ggc ctt caa gag gtt acg caa aac gtt   432
Ala Gly Thr Tyr Asn Phe Ala Gly Leu Gln Glu Val Thr Gln Asn Val
130                 135                 140 atc atc cca tac gtt gag tac gct aaa aca aaa ggc ctt tat gtt act   480
Ile Ile Pro Tyr Val Glu Tyr Ala Lys Thr Lys Gly Leu Tyr Val Thr
145                 150                 155                 160 ctt ggt ctt gac ttc acg ctt ctt aac gac cag gct act act caa tct   528
Leu Gly Leu Asp Phe Thr Leu Leu Asn Asp Gln Ala Thr Thr Gln Ser
                165                 170                 175 aac tta gac aag ttc aac gag atc tgg ggc tat ctt gct tca cgt ccg   576
Asn Leu Asp Lys Phe Asn Glu Ile Trp Gly Tyr Leu Ala Ser Arg Pro
            180                 185                 190 gag ctt cgc agc gct gac cac gtt atg ttt gag atc gta aac gag cct   624
Glu Leu Arg Ser Ala Asp His Val Met Phe Glu Ile Val Asn Glu Pro
        195                 200                 205 gta ctt tca tac gca aac ggt aaa tgg ggt ggc cat cca tct gac cca   672
Val Leu Ser Tyr Ala Asn Gly Lys Trp Gly Gly His Pro Ser Asp Pro
210                 215                 220 gac ttc gtt gac cac tgg aac gct ctt cgc gac ttc cag aac tct atc   720
Asp Phe Val Asp His Trp Asn Ala Leu Arg Asp Phe Gln Asn Ser Ile
225                 230                 235                 240 atc gca aca atc cgc aac caa ggc gct gac aac gtt atc tgg gca gct   768
Ile Ala Thr Ile Arg Asn Gln Gly Ala Asp Asn Val Ile Trp Ala Ala
                245                 250                 255 ggc ctt ggc tgg gac caa tac tac caa ctt tgc gca tct cac cca ctt   816
Gly Leu Gly Trp Asp Gln Tyr Tyr Gln Leu Cys Ala Ser His Pro Leu
            260                 265                 270 act gac cct ctt aac aac aca ggt tac gca gta cac tgg tat cct ggc   864
Thr Asp Pro Leu Asn Asn Thr Gly Tyr Ala Val His Trp Tyr Pro Gly
        275                 280                 285 tat ggc gca aac gac gac tat gct act ctt caa caa caa tgg gac aca   912
Tyr Gly Ala Asn Asp Asp Tyr Ala Thr Leu Gln Gln Gln Trp Asp Thr
290                 295                 300 aac atc aaa ccg tgc gca gac cat tac cct atc aac atc act gag acg   960
Asn Ile Lys Pro Cys Ala Asp His Tyr Pro Ile Asn Ile Thr Glu Thr
305                 310                 315                 320 act tgg tac aaa tgg caa cca ggc gac ccg gag tac tgg cac ctt ttt  1008
Thr Trp Tyr Lys Trp Gln Pro Gly Asp Pro Glu Tyr Trp His Leu Phe
```

```
                     325                 330                 335
gac gga acg aac gag ggc ttc ggc aag aac aca aaa gcg atc ttt acg      1056
Asp Gly Thr Asn Glu Gly Phe Gly Lys Asn Thr Lys Ala Ile Phe Thr
            340                 345                 350 gac gct ggc aac gta tct atc gcg gtt cat atg aac ggc ttc ctt ctt      1104
Asp Ala Gly Asn Val Ser Ile Ala Val His Met Asn Gly Phe Leu Leu
                355                 360                 365 gag cct ggc gta cgc tca act ttc gcg gac cct act gca ggc ctt aag      1152
Glu Pro Gly Val Arg Ser Thr Phe Ala Asp Pro Thr Ala Gly Leu Lys
    370                 375                 380 tac gac ggc gat ccg gct cgc gac gcg atg gct cgc ttc atc ttc gag      1200
Tyr Asp Gly Asp Pro Ala Arg Asp Ala Met Ala Arg Phe Ile Phe Glu
385                 390                 395                 400 tgg tac tat gaa cgc gca caa ctt tac ccg tgg aac ggc atc tgg aac      1248
Trp Tyr Tyr Glu Arg Ala Gln Leu Tyr Pro Trp Asn Gly Ile Trp Asn
                405                 410                 415 ggc atc cac aat ggc gct act tac aaa ctt cag aat cgc gca tct ggc      1296
Gly Ile His Asn Gly Ala Thr Tyr Lys Leu Gln Asn Arg Ala Ser Gly
            420                 425                 430 aaa atg atc gac gtt cct ggt ggc caa aac aac aac ggc ctt cag ctt      1344
Lys Met Ile Asp Val Pro Gly Gly Gln Asn Asn Asn Gly Leu Gln Leu
                435                 440                 445 caa caa tgg gct gac aac aac gct act gca cag caa tgg atc atc gac      1392
Gln Gln Trp Ala Asp Asn Asn Ala Thr Ala Gln Gln Trp Ile Ile Asp
    450                 455                 460 gac atg ggc acg tat aac aac ttc tat cgc ctt acg tca gta tca tct      1440
Asp Met Gly Thr Tyr Asn Asn Phe Tyr Arg Leu Thr Ser Val Ser Ser
465                 470                 475                 480 tca gac aac aag gta atg gac gta cgc aac ggt tct tct cac aac ggt      1488
Ser Asp Asn Lys Val Met Asp Val Arg Asn Gly Ser Ser His Asn Gly
                485                 490                 495 gag gcg atc caa ctt atg tct gac ttt ggc aac tca gcg caa caa ttc      1536
Glu Ala Ile Gln Leu Met Ser Asp Phe Gly Asn Ser Ala Gln Gln Phe
            500                 505                 510 cgc ctt atc cgc ctt tct aac ggc tac tgg agc atc ctt aac gtt aac      1584
Arg Leu Ile Arg Leu Ser Asn Gly Tyr Trp Ser Ile Leu Asn Val Asn
                515                 520                 525 tca aac aag gct gtt gag gtt aca ggc tct tca tct gcc gat ggc gct      1632
Ser Asn Lys Ala Val Glu Val Thr Gly Ser Ser Ser Ala Asp Gly Ala
    530                 535                 540 ctt ctt cag caa aac atg tat cgt ggc gac ctt cac caa cag tgg gac      1680
Leu Leu Gln Gln Asn Met Tyr Arg Gly Asp Leu His Gln Gln Trp Asp
545                 550                 555                 560 ctt atc cgc atc aac taa                                              1698
Leu Ile Arg Ile Asn
                565
```

<210> SEQ ID NO 12
<211> LENGTH: 565
<212> TYPE: PRT
<213> ORGANISM: Bacillus hemicellulosilyticus

<400> SEQUENCE: 12

```
Met Arg Glu Val Gly Arg Met Thr Lys Met Leu Leu Val Met Phe
1               5                   10                  15

Ile Val Pro Leu Leu Leu Ser Gly His Ser Ala Glu Ala Trp Thr Gly
                20                  25                  30

Met Pro Met Asp Lys Leu His Val Ser Gly Asn Gln Leu Val Asn Ser
            35                  40                  45
```

```
Ser Gly Gln Thr Val Leu Leu Asn Gly Trp His Gln Pro Ser Gly Ser
 50                  55                  60

Tyr Trp Thr Tyr Gln Gly Ser Asn Tyr Tyr Leu Asp Arg Asn Gly Gly
 65                  70                  75                  80

Asn Arg His Ala Ala Asn Leu Glu Tyr Leu Lys Asp Ile Ser Asp Thr
                 85                  90                  95

Phe Thr Asp Thr Ser Pro Lys Tyr Gly Asn Asp His Gly Trp Tyr Met
            100                 105                 110

Asn Gln Ile Arg Leu Phe Ile Asp Arg Glu Asp Met Gly Asp Val Ala
            115                 120                 125

Ala Gly Thr Tyr Asn Phe Ala Gly Leu Gln Glu Val Thr Gln Asn Val
        130                 135                 140

Ile Ile Pro Tyr Val Glu Tyr Ala Lys Thr Lys Gly Leu Tyr Val Thr
145                 150                 155                 160

Leu Gly Leu Asp Phe Thr Leu Leu Asn Asp Gln Ala Thr Thr Gln Ser
                165                 170                 175

Asn Leu Asp Lys Phe Asn Glu Ile Trp Gly Tyr Leu Ala Ser Arg Pro
            180                 185                 190

Glu Leu Arg Ser Ala Asp His Val Met Phe Glu Ile Val Asn Glu Pro
        195                 200                 205

Val Leu Ser Tyr Ala Asn Gly Lys Trp Gly Gly His Pro Ser Asp Pro
210                 215                 220

Asp Phe Val Asp His Trp Asn Ala Leu Arg Asp Phe Gln Asn Ser Ile
225                 230                 235                 240

Ile Ala Thr Ile Arg Asn Gln Gly Ala Asp Asn Val Ile Trp Ala Ala
            245                 250                 255

Gly Leu Gly Trp Asp Gln Tyr Tyr Gln Leu Cys Ala Ser His Pro Leu
        260                 265                 270

Thr Asp Pro Leu Asn Asn Thr Gly Tyr Ala Val His Trp Tyr Pro Gly
        275                 280                 285

Tyr Gly Ala Asn Asp Asp Tyr Ala Thr Leu Gln Gln Gln Trp Asp Thr
        290                 295                 300

Asn Ile Lys Pro Cys Ala Asp His Tyr Pro Ile Asn Ile Thr Glu Thr
305                 310                 315                 320

Thr Trp Tyr Lys Trp Gln Pro Gly Asp Pro Glu Tyr Trp His Leu Phe
            325                 330                 335

Asp Gly Thr Asn Glu Gly Phe Gly Lys Asn Thr Lys Ala Ile Phe Thr
        340                 345                 350

Asp Ala Gly Asn Val Ser Ile Ala Val His Met Asn Gly Phe Leu Leu
        355                 360                 365

Glu Pro Gly Val Arg Ser Thr Phe Ala Asp Pro Thr Ala Gly Leu Lys
    370                 375                 380

Tyr Asp Gly Asp Pro Ala Arg Asp Ala Met Ala Arg Phe Ile Phe Glu
385                 390                 395                 400

Trp Tyr Tyr Glu Arg Ala Gln Leu Tyr Pro Trp Asn Gly Ile Trp Asn
                405                 410                 415

Gly Ile His Asn Gly Ala Thr Tyr Lys Leu Gln Asn Arg Ala Ser Gly
        420                 425                 430

Lys Met Ile Asp Val Pro Gly Gly Gln Asn Asn Gly Leu Gln Leu
        435                 440                 445

Gln Gln Trp Ala Asp Asn Asn Ala Thr Ala Gln Gln Trp Ile Ile Asp
    450                 455                 460

Asp Met Gly Thr Tyr Asn Asn Phe Tyr Arg Leu Thr Ser Val Ser Ser
```

-continued

```
            465                 470                 475                 480
Ser Asp Asn Lys Val Met Asp Val Arg Asn Gly Ser Ser His Asn Gly
                    485                 490                 495

Glu Ala Ile Gln Leu Met Ser Asp Phe Gly Asn Ser Ala Gln Gln Phe
                500                 505                 510

Arg Leu Ile Arg Leu Ser Asn Gly Tyr Trp Ser Ile Leu Asn Val Asn
            515                 520                 525

Ser Asn Lys Ala Val Glu Val Thr Gly Ser Ser Ser Ala Asp Gly Ala
            530                 535                 540

Leu Leu Gln Gln Asn Met Tyr Arg Gly Asp Leu His Gln Gln Trp Asp
545                 550                 555                 560

Leu Ile Arg Ile Asn
                565
```